US006204007B1

(12) United States Patent
Owens et al.

(10) Patent No.: US 6,204,007 B1
(45) Date of Patent: *Mar. 20, 2001

(54) ANTIBODIES AGAINST E-SELECTIN

(75) Inventors: Raymond John Owens, Henley-on-Thames; Martyn Kim Robinson, Penn, both of (GB)

(73) Assignee: Celltech Therapeutics Limited (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,323

(22) PCT Filed: Mar. 28, 1995

(86) PCT No.: PCT/GB95/00692

§ 371 Date: Nov. 25, 1996

§ 102(e) Date: Nov. 25, 1996

(87) PCT Pub. No.: WO95/26403

PCT Pub. Date: Oct. 5, 1995

(30) Foreign Application Priority Data

Mar. 29, 1994 (GB) .................................... 9406243
Jul. 29, 1994 (GB) .................................... 9415331

(51) Int. Cl.$^7$ .............................. C12N 5/10; C12P 21/08; C07K 16/28
(52) U.S. Cl. ................ 435/69.1; 530/387.3; 530/388.22; 530/455
(58) Field of Search ............................ 530/388.22, 387.3; 435/172.3, 455, 69.1, 69.6

(56) References Cited

FOREIGN PATENT DOCUMENTS

| 0 323 806 A1 | 7/1989 | (EP) . |
| 0 438 312 A2 | 7/1991 | (EP) . |
| 0 307 434 B1 | 9/1993 | (EP) . |
| WO 87/04462 | 7/1987 | (WO) . |
| WO 88/07089 | 9/1988 | (WO) . |
| WO 90/07861 | 7/1990 | (WO) . |
| WO 91/09967 | 7/1991 | (WO) . |
| WO 91/09968 | 7/1991 | (WO) . |
| WO 92/11383 | 7/1992 | (WO) . |
| WO 93/22436 | 11/1993 | (WO) . |
| WO 94/29351 | 12/1994 | (WO) . |

OTHER PUBLICATIONS

Leeuwenberg, JFM et al. Transpl. Proc. 22(4):1991–1993, Aug. 1990.*
Lund, J et al. J. Immunol. 147(8):2657–2662, Oct. 1991.*
Gussow, D et al. Meth. Enzymol. 203:99–121, 1991.*
Angal et al., "A single amino acid substitution abolishes the heterogeneity of chimeric mouse/human (IgG4) antibody", *Mol. Immunol.*, 1993, 30(1), 105–108.

Bevilacqua et al., "Endothelial Leukocyte Adhesion Molecule 1: An Inducible Receptor for Neutrophils Related to Complement Regulatory Proteins and Lectins", *Science*, 1989, 243, 1160–1165.
Buist et al., "Kinetics and Tissue Distribution of the Radiolabeled Chimeric Monoclonal Antibody Mov18 IgG and F(ab')$_2$ Fragments in Ovarian Carcinoma Patients", *Cancer Res.*, 1993, 53, 5413–5418.
Burton et al., "Human Antibody Effector Function", *Adv. Immunol.*, Academic Press, 1992, 51, 1–84.
Burton et al., "The C1q receptor site on immunoglobulin G", *Nature*, 1980, 288, 338–344.
Burton, "Immunoglobulin G: Functional Sites", *Mol. Immunol.*, 1985, 22(3), 161–206.
Carter et al., "Humanization of an anti–p185$^{HER2}$ antibody for human cancer therapy", *Proc. Natl. Acad. Sci. USA*, 1992, 89, 4285–4289.
Chaiken et al., "Analysis of Macromolecular Interactions Using Immobilized Ligands", *Anal. Biochem.*, 1992, 201, 197–210.
Co et al., "Chimeric and Humanized Antibodies with Specificity for the CD33 Antigen", *J. Immunol.*, 1992, 148(4), 1149–1154.
Co et al., "Humanized antibodies for antiviral therapy", *Proc. Natl. Acad. Sci. USA*, 1991, 88, 2869–2873.
Cockett et al., "The use of engineered E1A genes to transactivate the hCMV–MIE promoter in permanent CHO cell lines", *Nucl. Acids Res.*, 1990, 19(2), 319–325.
Daugherty et al., "Polymerase chain reaction facilitates the cloning, CDR–grafting, and rapid expression of a murine monoclonal antibody directed against the CD18 component of leukocyte integrins", *Nucl. Acids Res.*, 1991, 19(9), 2471–2476.
Duncan et al., "Localization of the binding site for the human high–affinity Fc receptor on IgG", *Nature*, 1988, 332, 563–564.
*Editorials*, "Antibodies to endothelial cells", *Lancet*, 1991, 337, 649–650.
Gundel et al., "Endothelial Leukocyte Adhesion Molecule–1 Mediates Antigen–induced Acute Airway Inflammation and Late–phase Airway Obstruction in Monkeys", *J. Clin. Invest.*, 1991, 88, 1407–1411.
Jones et al., "Replacing the complementarity–determining regions in a human antibody with those from a mouse", *Nature*, 1986, 321, 522–525.

(List continued on next page.)

Primary Examiner—David Saunders
Assistant Examiner—F. Pierre VanderVegt
(74) Attorney, Agent, or Firm—Woodcock Washburn Kurtz Mackiewicz & Norris LLP

(57) ABSTRACT

This invention relates to whole antibodies of neutral isotype having specificity for E-selectin, process for their preparation (using vectors), pharmaceutical compositions containing them, and their use in therapy and diagnosis. Said antibodies are variants of natural antibodies altered in the F$_c$ region, especially in the CH$_2$ domain, so that the interactions with antibodies F$_c$ receptors and complement are very low.

13 Claims, 24 Drawing Sheets

OTHER PUBLICATIONS

Jones et al., "Materials and Methods: Rapid PCR–Cloning of Full–length Mouse Immunoglobulin Variable Regions", *BioTechnology*, 1991, 9, 88–89.

Kabat et al., in Sequences of Proteins of Immunological Interest, 5th Edition, United States Department of Health and Human Services, 1991.

Kabat et al., in Sequences of Proteins of Immunological Interest, 4th Edition, United States Department of Health and Human Services, 1987.

Kohler et al., "Derivation of specific antibody–producing tissue culture and tumor lines by cell fusion", *Eur. J. Immunol.*, 1976, 6, 511.

Kramer et al., "The gapped duplex DNA approach to oligonucleotide–directed mutation construction", *Nucl. Acids Res.*, 1984, 12(24), 9441–9456.

Leatherbarrow et al., "Effector Functions of a Monoclonal Aglycosylated Mouse IgG2a: Binding and Activation of Complement Component C1 and Interaction with Human Monocyte Fc Receptor", *Mol. Immunol.*, 1985, 22(4), 407–415.

Leeuwenberg et al., "Role of ELAM–1 in Adhesion of Monocytes to Activated Human Endothelial Cells", *Scant J. Immunol.*, 1992, 35, 335–341.

Molthoff et al., "Comparison of the pharmacokinetics, biodistribution and dosimetry of monoclonal antibodies OC125, OV–TL 3, and 139H2 as IgG and F(ab')$_2$ fragments in experimental ovarian cancer", *Br. J. Cancer*, 1992, 65, 677–683.

Morrison et al., "Chimeric human antibody molecules: Mouse antigen–binding domains with human constant region domains", *Proc. Natl. Acad. Sci. USA*, 1984, 81, 6851–6855.

Mulligan et al., "Role of Endothelial–Leukocyte Adhesion Molecule 1 (ELAM–1) in Neutrophil–mediated Lung injury in Rats", *J. Clinical Invest.*, 1991, 88, 1396–1406.

Picker et al., "ELAM–1 is an adhesion molecule for skin–homing T cells", *Nature*, 1991, 349, 796–799.

Pimm et al., "Blood and tissue kinetics of radiolabelled anti–CEA monoclonal antibody and F(ab)$_2$ and Fab fragments in nude mice with human tumour xenografts: implications for tumour imaging and radioimmunotherapy", *Nuclear Medicine Commun.*, 1989, 10, 589–593.

Podolsky et al., "Attenuation of Colitis in the Cotton–top Tamarin by Anti–α4 integrin Monoclonal Antibody", *J. Clin. Invest.*, 1993, 92, 372–380.

Queen et al., A humanized antibody that binds to the interleukin 2 receptor, *Proc. Natl. Acad. Sci. USA*, 1989, 86, 10029–10033.

Reichmann et al., "Reshaping human antibodies for therapy", *Nature*, 1988, 332, 323–327.

Routledge et al., "A humanized monovalent CD3 antibody which can activate homologous complement", *Eur. J. Immunol.*, 1991, 21, 2717–2725.

Verhoeyen et al., "Reshaping Human Antibodies: Grafting an Antilysozyme Activity", *Science*, 1988, 239, 1534–1536.

Westphal et al., "Anti–endothelial cell antibodies in sera of patients with autoimmune diseases: comparison between ELISA and FACS analysis", *Clin. Exp. Immunol.*, 1994, 96, 444–449.

Whittle et al., "Expression in COS cells of a mouse–human chimaeric B72.3 antibody", *Prot. Eng.*,1987, 1(6), 499–505.

Woof et al., "Localisation of the Monocyte–Binding Region on Human Immunoglobulin G", *Mol. Immunol.*, 1986, 23(3), 319–330.

Xu et al., "Residue at Position 331 in the IgG1 and IgG4 $C_H2$ Domains Contributes to Their Differential Ability to Bind and Activate Complement", *J. Biol. Chem.*, 1994, 269(5), 3469–3474.

Yan et al., "Human/Severe Combined Immunodeficient Mouse Chimeras", *J. Clin. Invest.*, 1993, 91, 986–996.

Yan et al., "Leukocyte Recruitment into Human Skin Transplanted onto Severe Combined Immunodeficient Mice Induced by TNF–α is Dependent on E–Selection", *J. Immunol.*, 1994, 152, 3053–3063.

* cited by examiner

FIG. 1a

LIGHT CHAIN VARIABLE DOMAIN.

```
ATG AGT GTG CCC ACT CAG GTC CTG GGG TTG CTG CTG CTG TGG CTT ACA GAT GCC
TAC TCA CAC GGG TGA GTC CAG GAC CCC AAC GAC GAC GAC ACC GAA TGT CTA CGG
 M   S   V   P   T   Q   V   L   G   L   L   L   L   W   L   T   D   A>

AGA TGT GAT ATC GTG ATG ACC CAG TCT CCC AAG TCC CTG TCT GTG ACA GCA GGA
TCT ACA CTA TAG CAC TAC TGG GTC AGA GGG TTC AGG GAC AGA CAC TGT CGT CCT
 R   C   D   I   V   M   T   Q   S   P   K   S   L   S   V   T   A   G>

GAG AAG GTC ACT ATG CGC TGC AAG TCC AGT CAG AGT CTG TTA AAC AGT GGA AAT
CTC TTC CAG TGA TAC GCG ACG TTC AGG TCA GTC TCA GAC AAT TTG TCA CCT TTA
 E   K   V   T   M   R   C   K   S   S   Q   S   L   L   N   S   G   N>

CAA CAG AAC TAC TTG ACT TGG TAC CGC CAG CCT GGA CCT CCT AAA CTT CTT GAA
GTT GTC TTG ATG AAC TGA ACC ATG GCG GTC GGA CCT GGA GGA TTT GAA GAA CTT
 Q   Q   N   Y   L   T   W   Y   Q   Q   P   G   P   P   K   L   L   E>
           G

TTG ATC TAT TGG GCA TCC ACT AGG GAA TCC GGG GTC CCT GAT CGC TTC ACA GGC
AAC TAG ATA ACC CGT AGG TGA TCC CTT AGG CCC CAG GGA CTA GCG AAG TGT CCG
 L   I   Y   W   A   S   T   R   E   S   G   V   P   D   R   F   T   G>
                 A

AGT GGA TCT GGA ACA GAT TTC ACT CTC ACC ATC AGC AGT GTG CAG ACT GAA GAC
TCA CCT AGA CCT TGT CTA AAG TGA GAG TGG TAG TCG TCA CAC GTC TGA CTT CTG
 S   G   S   G   T   D   F   T   L   T   I   S   S   V   Q   T   E   D>

CTG GCA GTT TAT TAC TGT CAG AAT GAT TAT ATA TAT CCG CTC ACG TTC GGT GCT
GAC CGT CAA ATA ATG ACA GTC TTA CTA ATA TAG GGC GAG TGC AAG CCA CGA CGA
 L   A   V   Y   Y   C   Q   N   D   Y   I   Y   P   L   T   F   G   A>

GGC ACC AAG CTG GAG CTG AAA ATC CGT
CCG TGG TTC GAC CTC GAC TTT TAG GCA
 G   T   K   L   E   L   K   I   R>
```

FIG. 1b

HEAVY CHAIN VARIABLE DOMAIN.

```
                              A                    G G
CCG CCA CC ATG GGA TGG AGC CCT GGG ATC TTT ATC TTC CTC CTC TCA GTA ATT
GGC GGT GG TAC CCT ACC TCG ACC TAA AAA TAG AAG GAG GAG AGT CAT TAA
        M   G   W   S   W   I   F   I   F   L   L   S   V   I>
                        G   V
                        G

GCA GGT GTC CAA TCC CAG GTT CAA CTG CAG TCT GGG ACT GAA CTG GTG
CGT CCA CAG GTT AGG GTC CAA GTT GAC GTC AGA CCC TGA CTT GAC CAC
 A   G   V   Q   S   Q   V   Q   L   Q   S   G   T   E   L   V>

AGG CCT GGG GCT TCA GTG ACG CTG TCC TGC AAG GCT TCG GGC TAC ACA TTT
TCC GGA CCC CGA AGT CAC TGC GAC AGG ACG TTC CGA AGC CCG ATG TGT AAA
 R   P   G   A   S   V   T   L   S   C   K   A   S   G   Y   T   F>

ACT GAC CAT GAA ATG CAC TGG GTG AAG CAG ACA CCT GGA CTT GGC CTG GAA
TGA CTG GTA CTT TAC GTG ACC CAC TTC GTC TGT GGA CCT GAA CCG GAC CTT
 T   D   H   E   M   H   W   V   K   Q   T   P   V   L   G   L   E>
         —————————————————
TGG ATT GGA ACT ATT GAT CCT GAA ACT GGT ACT GCC TAC AAT CAG AAG TTC
ACC TAA CCT TGA TAA CTA GGA CTT TGA CCA TGA CGG ATG TTA GTC TTC AAG
 W   I   G   T   I   D   P   E   T   G   T   A   Y   N   Q   K   F>
 ———————
TTC AAG GGC AAG GCC ACA CTG ACT GCA GAC AAA TCC TCC TCC ACA GCC TAC
AAG TTC CCG TTC CGG TGT GAC TGA CGT CTG TTT AGG AGG AGG TGT CGG ATG
 F   K   G   K   A   T   L   T   A   D   K   S   S   S   T   A   Y>
 ———
ATG GAC CTC CTC CGC GGC CTG ACA TCT GAG GAC TCT GCC GTC TAT TAC TGT
TAC CTG GAG GAG GCG CCG GAC TGT AGA CTC CTG AGA CGG CAG ATA ATG ACA
 M   D   L   L   R   G   L   T   S   E   D   S   A   V   Y   Y   C>

GTC CTA AGG ATG GAC TAC TGG GGT CAA GGA ACC TCA GTC ACC GTC TCC GCA
CAG GAT TCC TAC CTG ATG ACC CCA GTT CCT TGG AGT CAG TGG CAG AGG CGT
 V   L   R   M   D   Y   W   G   Q   G   T   S   V   T   V   S   A>
 ———————————————
```

FIG. 2a

Heavy chain variable domain.

```
GCG CGC AAG CTT GCC GCC ACC ATG GAA TGG AGC TGG GTC TTT CTC TTC
CGC GCG TTC GAA CGG CGG TGG TAC CTT ACC TCG ACC CAG AAA GAG AAG
                            M   E   W   S   W   V   F   L   F>

TTC CTG TCA GTA ACT ACA GGA GTC CAT TCT CAG GTG CAG CTG GTG CAG
AAG GAC AGT CAT TGA TGT CCT CAG GTA AGA GTC CAC GTC GAC CAC GTC
 F   L   S   V   T   T   G   V   H   S   Q   V   Q   L   V   Q>

TCT GGA GCA GAG GTG AAG AAG CCT GGA TCT TCT GTG AAG GTG TCT TGT
AGA CCT CGT CTC CAC TTC TTC GGA CCT AGA AGA CAC TTC CAC AGA ACA
 S   G   A   E   V   K   K   P   G   S   S   V   K   V   S   C>

AAG GCA TCT GGA TAC ACA TTC ACA GAC CAC GAG ATG CAC TGG GTG AGA
TTC CGT AGA CCT ATG TGT AAG TGT CTG GTG CTC TAC GTG ACC CAC TCT
 K   A   S   G   Y   T   F   T   D   H   E   M   H   W   V   R>

CAG GCA CCT GGA CAG GGA CTC GAG TGG ATT GGA ACA ATT GAC CCT GAG
GTC CGT GGA CCT GTC CCT GAG CTC ACC TAA CCT TGT TAA CTG GGA CTC
 Q   A   P   G   Q   G   L   E   W   I   G   T   I   D   P   E>

ACA GGA GGA ACA GCC TAC AAT CAG AAG TTC AAG GGA AGA GCA ACA CTG
TGT CCT CCT TGT CGG ATG TTA GTC TTC AAG TTC CCT TTT CGT TGT GAC
 T   G   G   T   A   Y   N   Q   K   F   K   G   R   A   T   L>

ACA GCA GAC AAG TCT ACG AAT ACC GCC TAC ATG GAG CTG TCT TCT CTG
TGT CGT CTG TTC AGA TGC TTA TGG CGG ATG TAC CTC GAC AGA AGA GAC
 T   A   D   K   S   T   N   T   A   Y   M   E   L   S   S   L>

AGA TCT GAG GAC ACA GCA GTG TAC TAC TGT ACA GTG CTC AGA ATG GAC
TCT AGA CTC CTG TGT CGT CAC ATG ATG ACA TGT CAC GAG TCT TAC CTG
 R   S   E   D   T   A   V   Y   Y   C   T   V   L   R   M   D>

TAC TGG GGA CAG GGA ACA CTG GTG ACA GTG TCT TCT
ATG ACC CCT GTC CCT TGT GAC CAC TGT CAC AGA AGA
 Y   W   G   Q   G   T   L   V   T   V   S   S
```

FIG. 2b

Light chain variable domain.

```
GGA CTG TTC GAA GCC GCC ACC ATG TCT GTC CCC ACC CAA GTC CTC GGA
CCT GAC AAG CTT CGG CGG TGG TAC AGA CAG GGG TGG GTT CAG GAG CCT
                            M   S   V   P   T   Q   V   L   G>

CTC CTG CTG CTG TGG CTT ACA GAT GCC AGA TGC GAT ATC CAG ATG ACT
GAG GAC GAC GAC ACC GAA TGT CTA CGG TCT ACG CTA TAG GTC TAC TGA
 L   L   L   L   W   L   T   D   A   R   C   D   I   Q   M   T>

CAG AGT CCA AGT ACT CTC AGT GCC AGT GTA GGT GAT AGG GTC ACC ATC
GTC TCA GGT TCA TGA GAG TCA CGG TCA CAT CCA CTA TCC CAG TGG TAG
 Q   S   P   S   T   L   S   A   S   V   G   D   R   V   T   I>

ACT TGT AAG TCT TCT CAA TCT CTC TTA AAC TCC GGT AAC CAG CAG AAC
TGA ACA TTC AGA AGA GTT AGA GAG AAT TTG AGG CCA TTG GTC GTC TTG
 T   C   K   S   S   Q   S   L   L   N   S   G   N   Q   Q   N>

TAC CTC ACT TGG TAC CAG CAG AAA CCA GGT AAA GCC CCA AAG CTC CTC
ATG GAG TGA ACC ATG GTC GTC TTT GGT CCA TTT CGG GGT TTC GAG GAG
 Y   L   T   W   Y   Q   Q   K   P   G   K   A   P   K   L   L>

ATC TAT TGG GCC TCT ACT AGG GAA TCT GGT GTA CCA GAT AGA TTC ACT
TAG ATA ACC CGG AGA TGA TCC CTT AGA CCA CAT GGT CTA TCT AAG TGA
 I   Y   W   A   S   T   R   E   S   G   V   P   D   R   F   T>

GGT AGT GGT AGT GGT ACT GAT TTC ACT CTC ACT ATC AGT AGT CTC CAG
CCA TCA CCA TCA CCA TGA CTA AAG TGA GAG TGA TAG TCA TCA GAG GTC
 G   S   G   S   G   T   D   F   T   L   T   I   S   S   L   Q>

CCA GAT GAT TTC GCC ACT TAT TAC TGT CAG AAC GAT TAC GAT TAC CCA
GGT CTA CTA AAG CGG TGA ATA ATG ACA GTC TTG CTA ATG CTA ATG GGT
 P   D   D   F   A   T   Y   Y   C   Q   N   D   Y   D   Y   P>

TTA ACT TTC GGT CAG GGT ACT AAA GTA GAA ATC AAA CGT
AAT TGA AAG CCA GTC CCA TGA TTT CAT CTT TAG TTT GCA
 L   T   F   G   Q   G   T   K   V   E   I   K   R
```

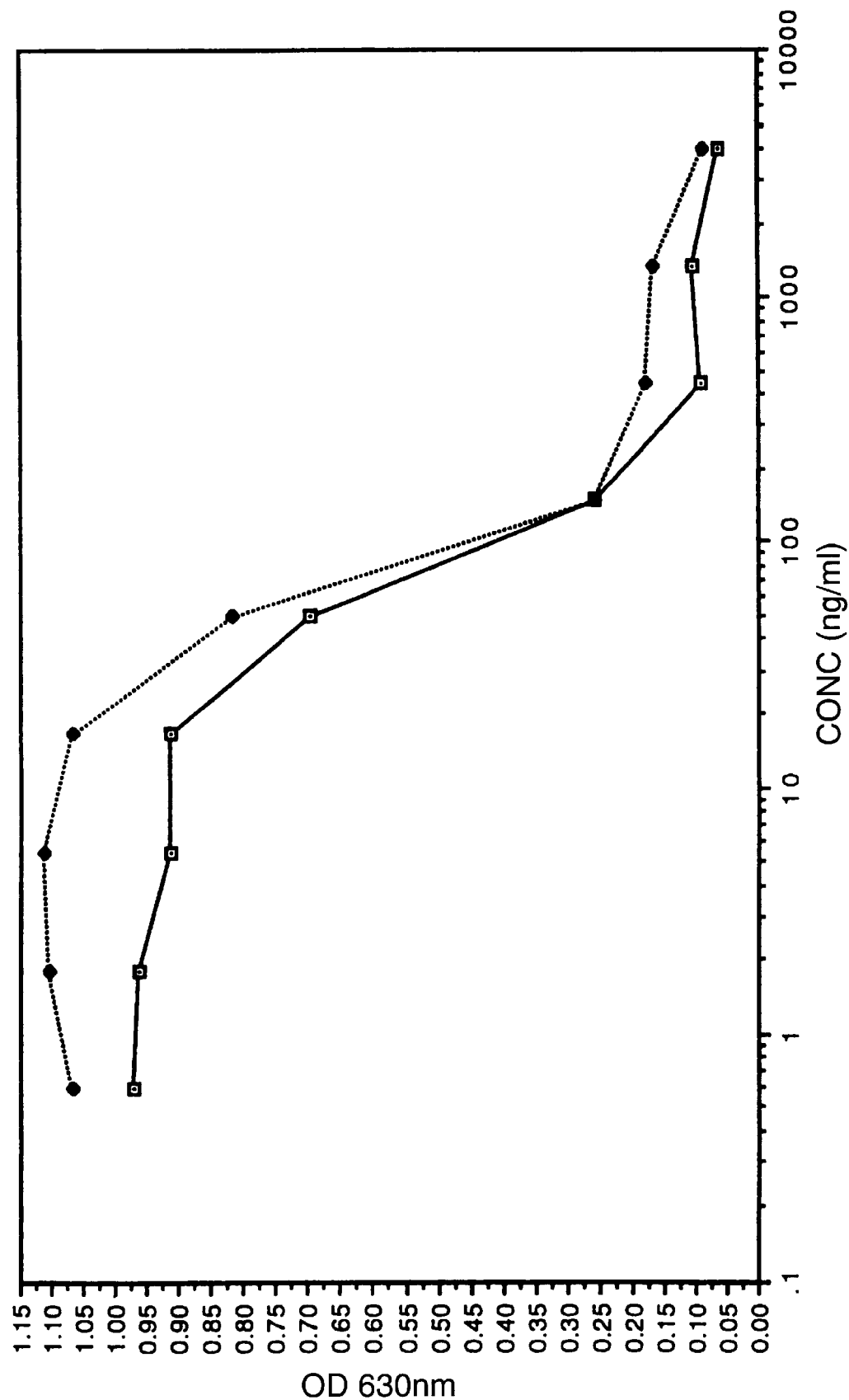

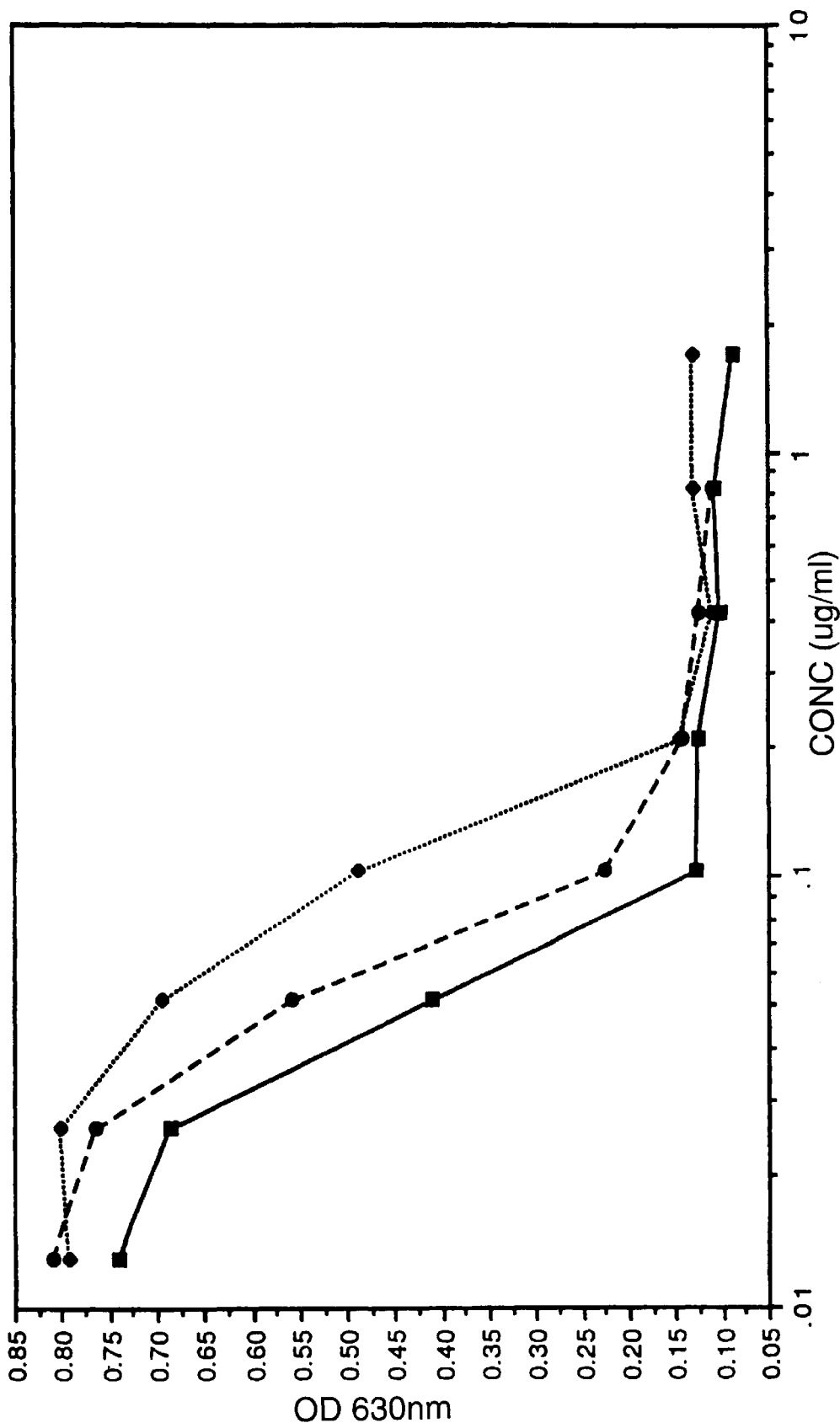

FIG. 5 Design of heavy chain FcR1 mutants.

[a] Sequences of the amino termini of human IgG CH2 domains.

```
                   235
G1    A P E L L G G P S V F L F P P K D T........
G2    A P P V A G . P S V F L F P P K D T........
G3    A P E L L G G P S V F L F P P K D T........
G4    A P E F L G G P S V F L F P P K D T........
```

[b] Sequences of mutagenic oligonucleotides.

```
Protein      A   P   E   F   I/A   G   G   P   S   V
                         V/T
```

Oligonucleotides

```
                                AC
5'        CCT GAG TTC GTC GGG GGA CCA TCA GTC TTC 3'
GA AGG AGT CGT GGA CTC AAG CAG CCC CCT GG
                                TG
```

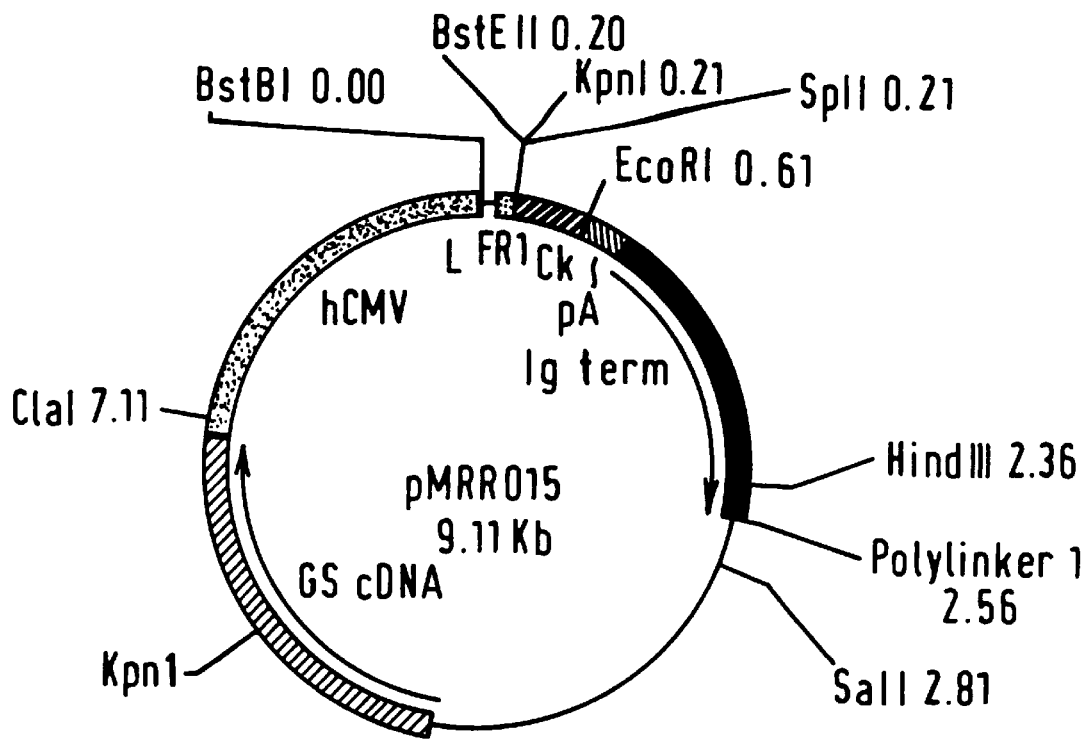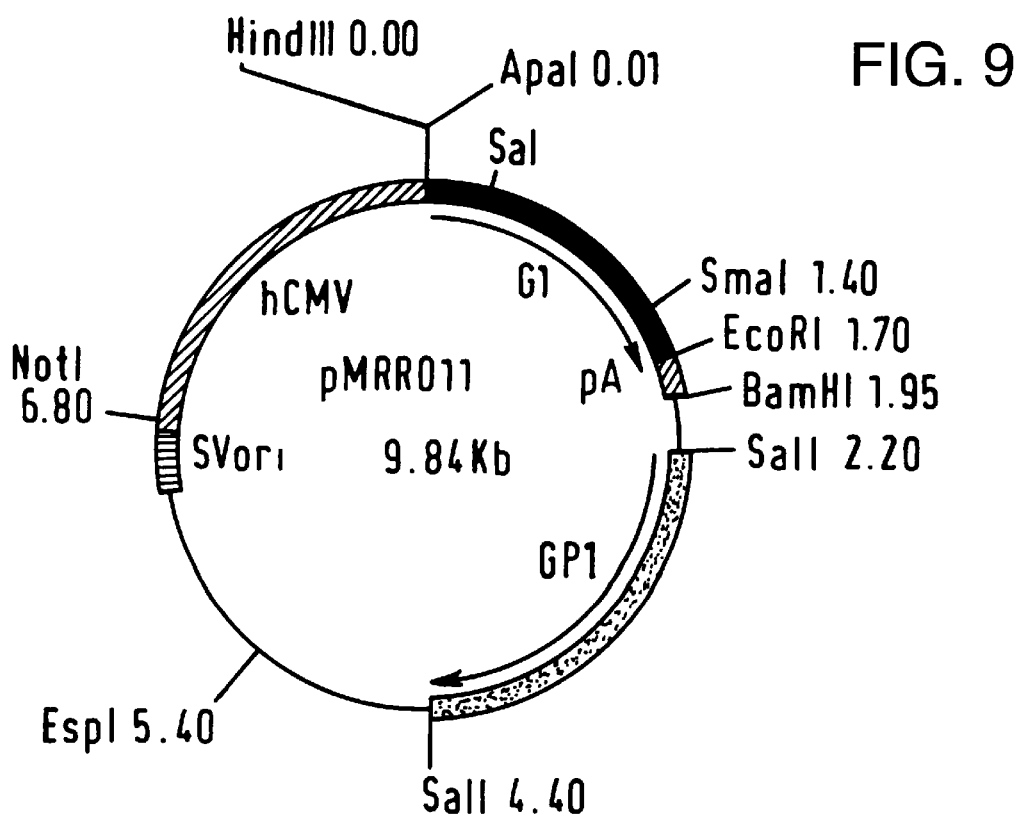
FIG. 9

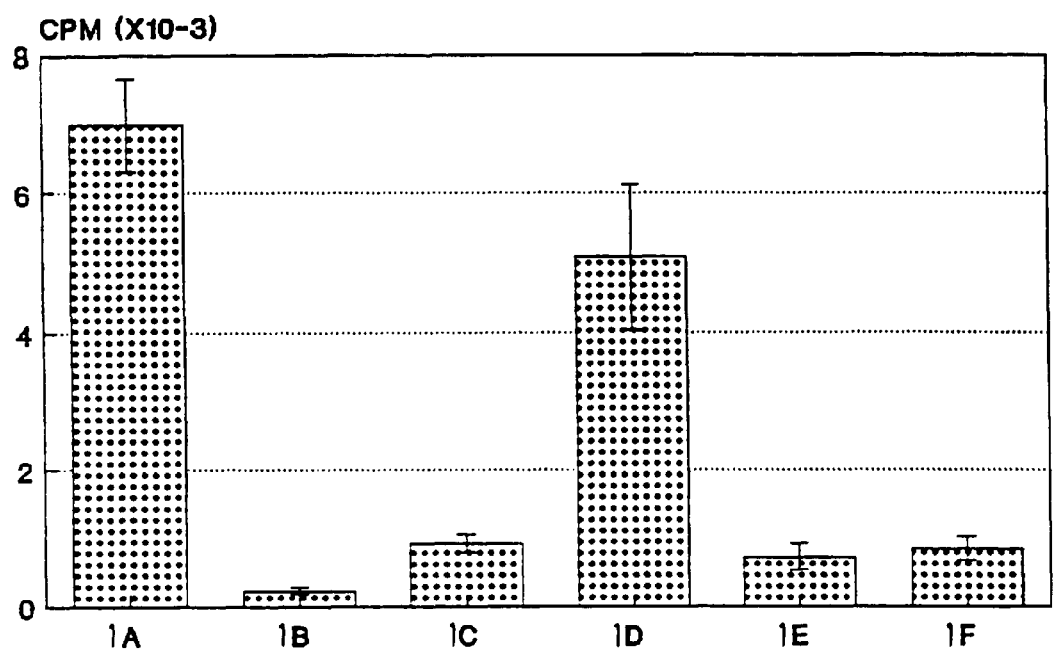
FIG. 17
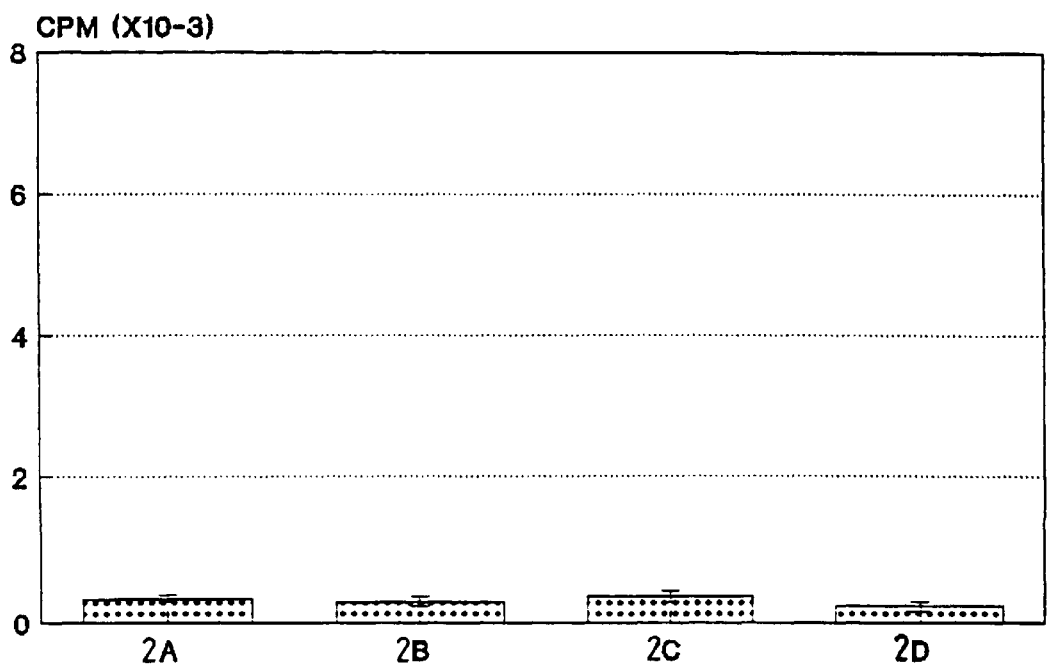

(A)

(B)

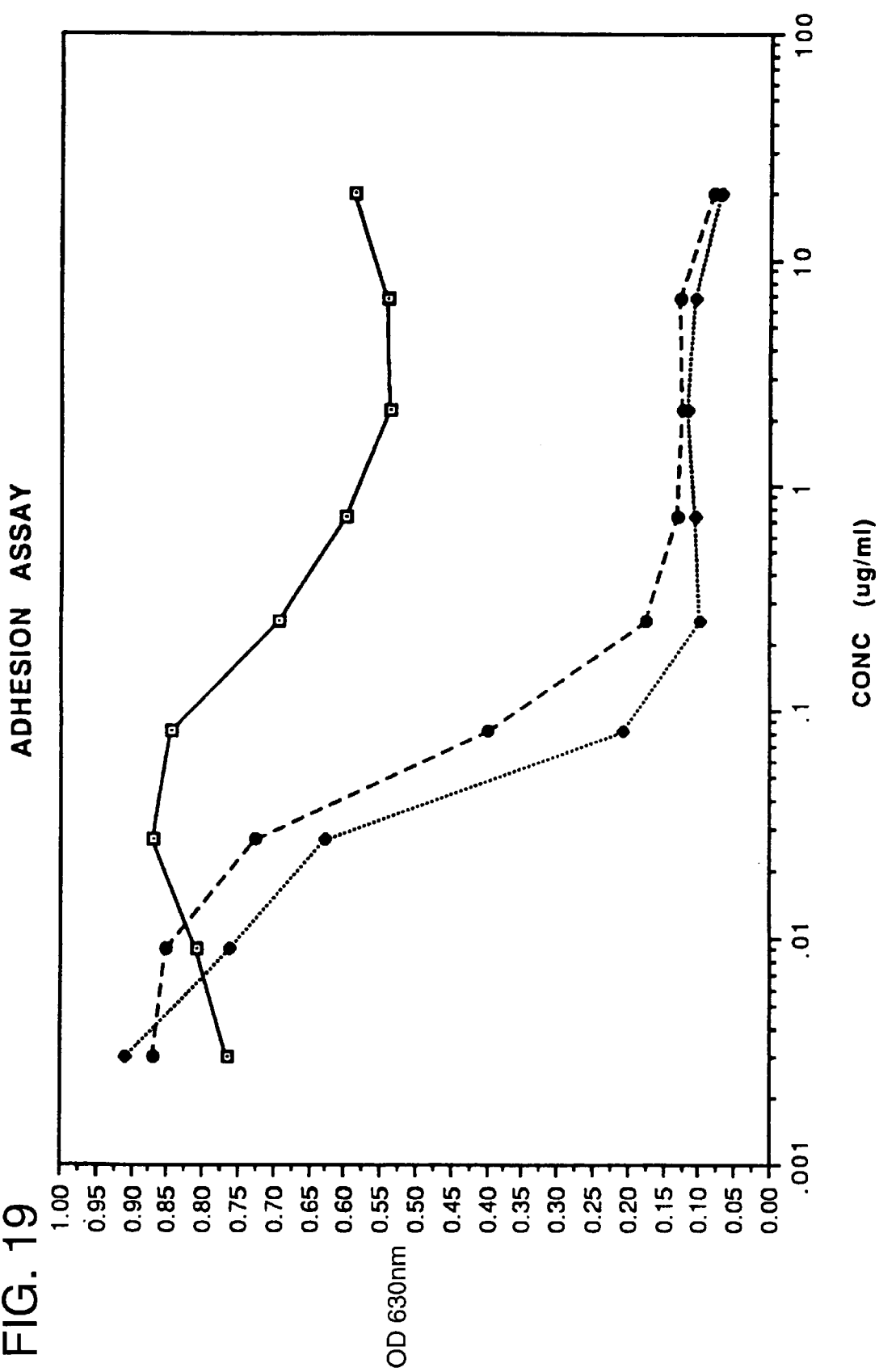

ANTIBODIES AGAINST E-SELECTIN

This application is a national phase of PCT/GB95/00692.

FIELD OF THE INVENTION

This invention relates to antibodies having specificity for E-selectin characterised in that said antibodies are whole antibodies of neutral isotype, to processes for preparing said antibodies, to pharmaceutical compositions containing said antibodies, and to medical uses of said antibodies.

BACKGROUND OF THE INVENTION

Selectins are a family of structurally related transmembrane glycoproteins implicated in the adhesion of leukocytes to vascular endothelial cells. The three known members, designated E-, P- and L- selectin are composed of three types of domain, an amino terminal C-type lectin domain, one EGF-like domain and between two and nine complementary regulatory repeats. Stimulation of endothelium by inflammatory cytokines e.g. II-1, or TNF results in the upregulation of E-selectin expression on the cell surface.

Experiments in vitro have shown that E-selectin can support the adhesion of polymorphonuclear cells, monocytes and a subpopulation of T-lymphocytes (see for example, Bevilacqua et al (1989) Science 243 1160–1165; Picker et al (1991) Nature 349 796–799 and Leeuwenberg et al (1992) Scant. J. Immunol 35 335–341). Mouse antibodies to E-selectin that block PMN binding in vitro have been shown to reduce extravasation of PMNs (neutrophils) in animal models (Mulligan, M. et al J. Clinical Investigation 88, 1396–1406 (1991) and Gundel, R. et al J. Clinical Investigation 88, 1407–1411 (1991)).

E-selectin thus appears to play a key role in the movement of leukocytes to sites of inflammation due to injury or infection. A corollary of this is that the expression of E-selectin is increased in certain inflammatory diseases. Hence E-selectin contributes to the disease process by supporting the adhesion of leukocytes which in turn cause tissue damage. It follows that an antibody to E-selectin that blocks this process would attenuate the extent or severity of the inflammation and hence be of therapeutic benefit.

Since most available monoclonal antibodies are of rodent origin, they are naturally antigenic in humans and thus can give rise to an undesirable immune response termed the HAMA (Human Anti-Mouse Antibody) response. Therefore, the use of rodent monoclonal antibodies as therapeutic agents in humans is inherently limited by the fact that the human subject will mount an immunological response to the antibody and will either remove it entirely or at least reduce its effectiveness.

Proposals have been made for making non-human MAbs less antigenic in humans using engineering techniques. These techniques generally involve the use of recombinant DNA technology to manipulate DNA sequences encoding the polypeptide chains of the antibody molecule. A simple form of engineering antibodies involves the replacement of the constant regions of the murine antibody with those from a human antibody (Morrison et al (1984) Proc. Natl. Acad. Sci. USA 81 6851–55; Whittle et al (1987) Prot. Eng. 1 499–505). The lowering of the level of the HAMA response to the chimeric antibodies leads to the expectation that further engineering of the variable region outside of the antigen binding site may abolish the response to these regions and further reduce any adverse response.

A more complex form of engineering of an antibody involves the redesign of the variable region domain so that the amino acids constituting the murine antibody binding site are integrated into the framework of a human antibody variable region. This has led to the reconstitution of full antigen binding activity in a number of cases (Co et al (1990) J. Immunol. 148 1149–1154; Co et al (1992) Proc. Natl. Acad. Sci. USA 88 2869–2873; Carter et al (1992) Proc. Natl. Acad. Sci. 89 4285–4289; Routledge et al (1991) Eur. J. Immunol. 21 2717–2725 and International Patent Specifications Nos. WO 91/09967; WO 91/09968 and WO 92/11383).

Naturally occurring and engineered human antibodies may be regarded as bifunctional agents, with the N-terminal variable region responsible for antigen binding and sequences within the C-terminal part responsible for determining interactions with the various cell types which participate in immune responses. Recognition of these effector sites on antibodies by specific cell surface receptors on cytotoxic cells can result in antibody-dependent cellular cytotoxicity and complement mediated lysis. This can result in killing of the cell presenting the antigen.

E-selectin is expressed on the surface of endothelial cells. The loss of endothelial cells as a result of antibody bound to target antigen is highly undesirable. Endothelial cells make up the endothelium which forms a barrier between the tissues of the body and the vascular system. The loss of or damage to the structural integrity of the endothelium is extremely disadvantageous and can lead to oedema and vasculitis. It is highly advantageous therefore to avoid depletion of the endothelial cell population while blocking the target antigen. Recent papers by Podolsky et al (J. Clin. Invest. 92 (1993) 372–380), Westphal et al Clin. Exp. Immunol. 96 444–449 (1994), and the Editorial Lancet 337 (1991) confirm that the use of whole antibody is undesirable due to undesirable effector functions mediated via the Fc region of the antibody. Another group has attempted to overcome the problem of undesirable effector functions by the use of antibody fragments lacking the effector signals which result in antibody-dependent cellular cytotoxicity (Mulligan et al J. Clinical Investigation 88, 1396–1406 (1991)). Antibody fragments are known, however, to have a short half-life (Pimm et al Nuclear Medicine Communication 10, 585–593 (1989); Molthoff et al Br. J. Cancer 65, 677–683 (1992) and Buist et al Cancer Res. 53 5413–5418 (1993)) making their therapeutic usefulness in the treatment of many diseases extremely limited.

BRIEF SUMMARY

The present invention provides a novel solution to this problem of preventing depletion of the target endothelial cell population. We have found that by making a whole anti-E-selectin antibody of neutral isotype it is possible to produce a therapeutically useful antibody which does not result in endothelial cell depletion.

In a first aspect the invention therefore provides an antibody having specificity for E-selectin characterised in that said antibody is a whole antibody of neutral isotype.

In a preferred embodiment of the first aspect of the invention the antibody has specificity for human E-selectin.

The antibodies according to the invention preferably recognise the E-selectin lectin or EGF domain.

As used herein the term 'whole' antibody is used to denote an antibody comprising substantially full length heavy and light chains, and antibodies to which amino acids have been substituted, altered, added and/or deleted.

The approach of using a whole antibody of neutral isotype has not been tried before in this area. The term 'neutral isotype' means that the interactions with antibody Fc receptors i.e. FcRI, FcRII and FcRIII and complement are absent or so weak as to cause minimal detrimental physiological effects such as antibody dependent cellular cytotoxicity (ADCC) and/or complement mediated lysis and also the antibody produces a minimal immune response in the host. As used herein the term 'minimal immune response' is used to denote a typical primate immune response to an iv injection of a human or engineered human antibody.

Anti-E-selectin antibody may be prepared using well-known immunological techniques employing E-selectin as antigen. Any suitable host may, for example, be immunised with E-selectin or activated HUVEC (human umbilical vein endothelial cells) and splenocytes or lymphocytes recovered and immortalised using for example the method of Kohler et al, Eur. J. Immunol. 6, 511 (1976). The resulting cells are diluted and cloned to obtain a single genetic line producing anti-E-selectin antibodies in accordance with conventional practice. Where it is desired to produce recombinant anti-E-selectin antibodies these may be produced using methods well known in the art.

Several regions of the Fc region of antibodies have been implicated in modulating effector functions (see for example European Patent No. 307434B and Lund et al (1991) J. Immunol. 147 2657–2662). For example Lund et al (1991) and other groups have implicated Leu 235 in the CH2 domain of human IgG3 heavy chain in binding of antibody to the high affinity receptor on mononuclear phagocytes (FcRI). Thus by altering this residue it is possible to produce an antibody lacking FcRI binding activity.

In a further aspect the invention provides an antibody characterised in that said antibody is a whole antibody of neutral isotype having specificity for E-selectin wherein one or more amino acid residues in the Fc region of said antibody has been altered from that in the naturally occurring sequence.

In a preferred embodiment of this aspect the invention therefore provides an antibody characterised in that said antibody is a whole antibody of neutral isotype having specificity for E-selectin wherein one or more amino acid residues in the Fc region of said antibody including residue 235 in the CH2 domain has been altered from that in the naturally occurring sequence.

Residue 235 occurs in the N-terminal region of the $CH_2$ domain of the heavy chain. We have found altering the naturally occurring residue e.g. residue Leu 235 to an alanine is particularly advantageous since the conservative nature of the amino acid change is less likely to produce undesirable structural changes in the molecule, which may result in the antibody being immunogenic.

In a preferred embodiment the antibody of the invention has an alanine residue at position 235 in the $CH_2$ domain and in a particularly preferred embodiment the antibody has a human γ4 isotype.

Alteration of antibody side chain interaction with FcR1 receptor may similarly be achieved by replacing leucine with isoleucine, valine, threonine or glutamic acid. It will be readily apparent to one skilled in the art that a number of other substitutions are possible within the overall aim of not introducing any undesirable structural changes in the molecule, which may lead to immunogenicity.

Where the antibody has isotypes such as human $\gamma_1$, $\gamma_2$ or $\gamma_3$ it will be apparent to one skilled in the art that further alterations to amino acid residues will be required to alter FcRI, FcRII and FcRIII binding where appropriate and also to minimise complement fixation. For example, alteration of residues 235 and 234 of the heavy chain of $\gamma_1$, and $\gamma_3$ antibodies is known to affect FcRI and FcRII binding (Burton and Woof Adv. Immunol (1992) 1: Academic Press), and similarly amino acid residues 234, 235, 330, 331, 318, 320 and 322 have been shown to be involved in binding and activation of complement (Xu et al (1994) J. Biol. Chem 269 (5) 3469–3474, Published European Patent No. EP 307434B and published International Patent Application No. WO 9429351). See also, Woof et al Mol. Immunol 23 319–330 (1986), Burton et al Nature 288 338–44 (1980); Burton Mol. Immunol 22 161–206 (1988); Leatherbarrow et al Mol. Immunol 22 407–415 (1985); and Duncan et al Nature 332 563–4 (1988). The antibodies of the invention preferably have a human isotype.

The standard techniques of molecular biology may be used to prepare DNA sequences coding for the antibodies according to the invention. Desired DNA sequences may be synthesised completely or in part using oligonucleotide synthesis techniques. Site-directed mutagenesis and polymerase chain reaction (PCR) techniques may be used as appropriate.

Suitable processes which may be used to alter the residue at position 235 include the PCR strand overlap procedure PCR mutagenesis, as described for example in the teaching of PCR Technology Principles and Applications for DNA Amplification (1989), Ed. H. A. Erlich, Stockton Press, N.Y., London, and oligonucleotide directed mutagenesis (Kramer et al, (Nucleic. Acid. Res. 12, 9441 (1984)). Suitable methods are also disclosed in Published European Patent No. EP307434B.

The alteration at position 235 or any other position of the molecule may be introduced at any convenient stage in the antibody production process. For example, where the antibody is a CDR-grafted antibody, the change may be made before, or more conveniently after CDR-grafting has been completed. This is described in more detail in the accompanying examples.

In a preferred embodiment the antibody molecule of the invention is an IgG and most preferably has a human γ4 isotype.

It has further been found (Angal et al (1993) Molecular Immunol 30 105–108) that the sequence of the hinge region of antibodies of the γ4 isotype, i.e. Cys-Pro-Ser-Cys can give rise to alternative forms of the antibody in association with correctly folded and assembled forms. This can be overcome by altering the Ser residue at position 228 to a Pro residue using for example site directed or oligonucleotide directed mutagenesis. The anti-E selectin antibodies of the invention which are of γ4 isotype preferably have the sequence Cys-Pro-Pro-Cys at the hinge region, and most preferably also have an alanine residue at position 235 in the CH2 domain.

The residue numbering used herein is according to the EU index described in Kabat et al [(1991) in: Sequences of Proteins of Immunological Interest, 5th Edition, United States Department of Health and Human Services].

The antibodies of the invention are preferably engineered human antibodies, most preferably CDR-grafted antibodies.

In a preferred embodiment the invention therefore provides an engineered human antibody having specificity for E-selectin characterised in that said antibody is a whole antibody of neutral isotype.

The term engineered human antibody molecule is used to describe a molecule having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains.

The whole anti-E-selectin antibodies of neutral isotype according to the invention are preferably engineered human antibodies wherein one or more amino acid residues in the Fc region of the antibody has been altered from that in the naturally occurring sequence.

The present invention provides an engineered human antibody molecule having specificity for E-selectin characterised in that said antibody is a whole antibody of neutral isotype and has an antigen binding site wherein at least one of the complementarity determining regions of the variable domain is derived from a non-human monoclonal antibody and the remaining immunoglobulin-derived parts of the engineered human antibody molecule are derived from a human immunoglobulin.

The engineered human antibody molecule may comprise a chimeric antibody or a CDR-grafted antibody. When the engineered human antibody molecule comprises a CDR-grafted antibody, the heavy and/or light chain variable domains may comprise only one or two non-human derived CDRs; though preferably all three heavy and light chain CDRs are derived from the non-human antibody.

The non-human antibody is preferably ENA-2. ENA-2 is a mouse IgG1/kappa antibody that binds to the lectin/EGF region of human E-selectin and blocks cell binding. (Leeuwenberg et al (1990) Transplantation Proceedings 22 (4) 1991–1993).

The human immunoglobulin derived parts of the engineered human antibody molecule may be derived from any suitable human immunoglobulin. For instance where the engineered human antibody molecule is a CDR-grafted antibody molecule, appropriate variable region framework sequences may be used having regard to class/type of the donor antibody from which the antigen binding regions are derived. Preferably the type of human framework used is of the same/similar class/type as the donor antibody. Advantageously the framework is chosen to maximise/optimise homology with the donor antibody sequence particularly at positions spacially close or adjacent to the CDRs. Examples of human frameworks which may be used to construct CDR-grafted antibodies are LAY, POM, TUR, TEI, KOL, NEWM, REI and EU; for instance KOL and NEWM for the heavy chain and REI for the light chain and EU for both the heavy chain and light chain.

In a preferred method the human frameworks are chosen by comparing the sequences of the donor and acceptor heavy and light chains and choosing the human framework sequence which is most homologous to the donor antibody.

The ENA-2 Vh domain shows closest sequence homology to group 1 human heavy chains and consequently the group 1 human antibody Eu was chosen as the framework for both the heavy and light chain variable domains.

The light or heavy chain variable domains of the engineered human antibody molecule may be fused to human light or heavy chain constant domains as appropriate, (the term Fc region and 'heavy chain constant domains' as used herein are to be understood to include hinge regions unless specified otherwise). The human constant domains of the engineered human antibody molecule, where present, may be selected having regard to the proposed function of the antibody, in particular the lack of effector functions which may be required.

For example, the heavy chain constant domains fused to the heavy chain variable region may be human IgA, IgG or IgM domains. Preferably human IgG domains are used. Depending on the choice of human constant domains it may be necessary to alter specific amino acid residues to remove any undesirable effector function in order to produce an antibody of neutral isotype by, for example, using site directed or oligonucleotide directed mutagenesis. Light chain human constant domains which may be fused to the light chain variable region include human Lambda or human Kappa chains.

Analogues of human constant domains may alternatively be advantageously used. These include those constant domains containing one or more additional amino acids than the corresponding human domain or those constant domains wherein one or more existing amino acids of the corresponding human domain has been substituted, added, deleted or altered. Such domains may be obtained, for example, by oligonucleotide directed mutagenesis.

Also human constant region domains of the engineered human antibody molecule may be selected having regard to the neutral isotype required for the antibody as defined previously.

By appropriate choice of immunoglobulin isotype it is possible to produce an antibody where antibody dependent complement fixation and where interaction with FcRI, FcRII and FcRIII are minimised e.g. by choosing a human γ4 isotype.

The invention further provides a process for the production of an antibody having specificity for E-selectin characterised in that said antibody is a whole antibody of neutral isotype which process comprises:
a) producing in an expression vector an operon having a DNA sequence which encodes said antibody heavy or light chain;
b) producing in an expression vector an operon having a DNA sequence which encodes a complementary antibody heavy or light chain;
c) transfecting a host cell with both operons and
d) culturing the transfected cell line to produce the antibody.

According to a preferred embodiment of this aspect of the invention there is provided a process for producing an engineered human antibody having specificity for E-selectin characterised in that said antibody is a whole antibody of neutral isotype which process comprises:
a) producing in an expression vector an operon having a DNA sequence which encodes an antibody heavy or light chain comprising a variable domain wherein at least one of the CDRs of the variable domain is derived from a non-human immunoglobulin and the remaining immunoglobulin-derived parts of the antibody chain are derived from a human immunoglobulin;
b) producing in an expression vector an operon having a DNA sequence which encodes a complementary antibody light or heavy chain comprising a variable domain wherein at least one of the CDRs of the variable domain is derived from a non-human immunoglobulin and the remaining immunoglobulin-derived parts of the antibody chain are derived from a human immunoglobulin;
c) transfecting a host cell with both operons; and
d) culturing the transfected cell line to produce the engineered human antibody molecule.

The CDRs of the variable domain are preferably derived from the same non-human immunoglobulin which is most preferably ENA-2.

In a particularly preferred embodiment of this aspect of the invention, at least one of the expression vectors contains a DNA sequence encoding an antibody heavy chain wherein one or more amino acid residues in the Fc region of said antibody most preferably including residue 235 in the CH2 domain has been altered from that in the naturally occurring sequence The change at amino acid residue 235 or at any other position may also be made after the whole antibody has been assembled using techniques such as site directed mutagenesis.

The cell line may be transfected with two vectors, the first vector containing the operon encoding the light chain-derived polypeptide and the second vector containing the operon encoding the heavy chain derived polypeptide. Preferably the vectors are identical except in so far as the coding sequences and selectable markers are concerned so as to ensure as far as possible that each polypeptide chain is equally expressed.

Alternatively, a single vector may be used, the vector including a selectable marker and the operons encoding both light chain- and heavy chain-derived polypeptides.

In further aspects, the invention also includes DNA sequences coding for the heavy and light chains of the antibodies of the present invention, cloning and expression vectors containing these DNA sequences, host cells transformed with these DNA sequences and processes for producing the heavy or light chains and antibody molecules comprising expressing these DNA sequences in a transformed host cell.

The general methods by which the vectors may be constructed, transfection methods and culture methods are well known per se (see for example Maniatis et al (1982) (Molecular Cloning, Cold Spring Harbor, N.Y.) and Primrose and Old (1980) (Principles of Gene Manipulation, Blackwell, Oxford) and the examples hereinafter).

The DNA sequences which encode the ENA-2 heavy and light chain variable domain amino acid sequences (and the corresponding deduced amino acid sequences) are given hereafter in FIG. 1.

DNA coding for human immunoglobulin sequences may be obtained in any appropriate way. For example, amino acid sequences of preferred human acceptor frameworks such as, LAY, POM, KOL, REI, EU, TUR, TEI and NEWM are widely available to workers in the art.

The standard techniques of molecular biology may be used to prepare DNA sequences coding for CDR-grafted products. Desired DNA sequences may be synthesised completely or in part using oligonucleotide synthesis techniques. Site-directed mutagenesis and polymerase chain reaction (PCR) techniques may be used as appropriate. For example, oligonucleotide directed synthesis (Jones et al (1986) Nature 321 522–525). Also oligonucleotide directed mutagenesis of a pre-existing variable domain region (Verhoeyen et al (1988) Science 1534–1536; Reichmann et al (1988) Nature 332 323–327).

Enzymatic filling-in of gapped oligonucleotides using T4 DNA polymerase (Queen et al (1989) Proc. Natl. Acad. Sci. USA 86 10029–10033; International Patent Application No. WO 90/07861) may be used.

Any suitable host cell/vector system may be used for expression of the DNA sequences coding the antibody heavy and light chains e.g. for the chimeric or CDR-grafted heavy and light chains. Bacterial e.g. *E. coli* and other microbial systems may be used. Eucaryotic e.g. mammalian host cell expression systems may also be used to obtain antibodies according to the invention, particularly for production of larger chimeric or CDR-grafted antibody products. Suitable mammalian host cells include CHO cells and myeloma or hybridoma cell lines, for example NSO cells. NSO cells are particularly preferred.

In the engineered human antibody according to the invention, the heavy and light chain variable domains may comprise either the entire variable domains of a non-human antibody such as the murine antibody ENA-2, or may comprise framework regions of a human variable domain having grafted thereon one, some or all of the CDRs of a non-human antibody such as the murine antibody ENA-2. Thus the engineered human antibody may comprise a chimeric engineered human antibody or a CDR-grafted engineered human antibody.

When the engineered human antibody is a CDR-grafted antibody, in addition to the CDRs, specific variable region framework residues may be altered to correspond to non-human e.g. ENA-2 mouse residues. Preferably the CDR-grafted antibodies of the present invention include CDR-grafted antibodies as defined in our International Patent Specification No. WO-A-91/09967. The disclosure of WO-A-91/09967 is incorporated herein by reference.

Preferably the CDRs of the heavy chain correspond to the Kabat defined MAb ENA-2 CDRs at all of CDR1 (31 to 35), CDR2 (50 to 65) and CDR3 (95 to 102). In addition the heavy chain may have mouse ENA-2 residues at one or more of residues 48, 67, 69, 73, 93 and 94. Similarly the light chain may have mouse ENA2 residues at positions 48, 60, 63, 70, 111 and 113.

The present invention also includes therapeutic and diagnostic compositions comprising the antibodies of the invention and the uses of these products and the compositions in therapy and diagnosis. Such compositions typically comprise an antibody according to the invention together with a pharmaceutically acceptable excipient, diluent or carrier, e.g. for in vivo use.

Thus in a further aspect the invention provides a therapeutic or diagnostic composition comprising an antibody according to the invention in combination with a pharmaceutically acceptable excipient, diluent or carrier.

The invention also provides a process for the preparation of a therapeutic or diagnostic composition comprising admixing an antibody according to the invention together with a pharmaceutically acceptable excipient, diluent or carrier.

The antibody may be the sole active ingredient in the therapeutic or diagnostic composition or may be accompanied by one or more other active ingredients. The therapeutic and diagnostic compositions may be in unit dosage form, in which case each unit dose comprises an effective amount of the antibody of the invention.

Furthermore, the invention also provides methods of therapy and diagnosis comprising administering an effective amount of an antibody according to the invention to a human or animal subject.

The antibodies and compositions may be for administration in any appropriate form and amount according to the therapy in which they are employed.

The therapeutic or diagnostic composition may take any suitable form for administration, and, preferably is in a form suitable for parenteral administration e.g. by injection of infusion, for example by bolus injection or continuous infusion. It may for example be administered intravenously, intramuscularly, intradermally or intraperitoneally. Where the product is for injection or infusion, it may take the form of a suspension, solution or emulsion in an oily or aqueous vehicle and it may contain formulatory agents such as suspending, preservative, stabilising and/or dispersing agents.

Alternatively, the antibody or composition may be in dry form, for reconstitution before use with an appropriate sterile liquid. The antibody may also be formulated for topical administration.

If the antibody or composition is suitable for oral administration, the formulation may contain, in addition to the active ingredient, additives such as: starch—e.g. potato, maize or wheat starch or cellulose—or starch derivatives such as microcrystalline cellulose; silica; various sugars such as lactose; magnesium carbonate and/or calcium phosphate. It is desirable that, if the formulation is for oral administration it will be well tolerated by the patient's digestive system. To this end, it may be desirable to include in the formulation mucus formers and resins. It may also be desirable to improve tolerance by formulating the antibody or compositions in a capsule which is insoluble in the gastric juices. It may also be preferable to include the antibody or composition in a controlled release formulation.

In a still further aspect of the invention, there is provided a method of treatment of a human or animal subject suffering from or at risk of a disorder associated with increased E-selectin expression the method comprising administering to the subject an effective amount of the antibody or composition of the invention. In particular, the human or animal subject may be suffering from an inflammatory disorder such as a skin disorder e.g. psoriasis.

The antibodies of the invention are particularly useful in the treatment of inflammatory diseases generally. They are particularly useful in the treatment of inflammatory skin diseases e.g. psoriasis, contact dermatitis and eczema; inflammatory bowel disease e.g. Crohn's disease and ulcerative colitis, in lung inflammatory disorders, e.g. ARDS; arthritis, e.g. rheumatoid arthritis; vasculitis, liver disease e.g. alcoholic hepatitis and cirrhosis; and thermal trauma.

Therapeutic and diagnostic uses typically comprise administering an effective amount of an antibody according to the invention to a human subject. The exact dose to be administered will vary according to the use of the antibody and on the age, sex and condition of the patient but may typically be varied from about 0.1 mg to 1000 mg for example from about 1 mg to 500 mg. The antibody may be administered as a single dose or in a continuous manner over a period of time. Varying doses may be repeated as appropriate. The antibody may be formulated in accordance with conventional practice for administration by any suitable route and may generally be in a liquid form (e.g. a solution of the antibody in a sterile physiologically acceptable buffer) for administration by for example an intravenous, intraperitoneal or intramuscular route.

Since the whole antibodies are of neutral isotype the interaction with Fc receptors will be minimal. This has the effect that such an antibody should block greater than 80% of human neutrophil binding to E-selectin in an in vitro assay and furthermore that this may be observed irrespective of the FcR status of the donor. We believe this may be a considerable advantage in that the antibody is suitable for administration to all patients thereby avoiding the necessity of determining the FcR status of the patient prior to administration of the antibody.

The antibodies according to the invention in in vitro assays show minimal binding to FcR1 carrying cells that do not express E-selectin thereby minimising the potential for ADCC.

The antibody according to the invention may also be used for inflamed site-specific delivery of drugs, nucleic acid and proteins and fragments thereof, radionuclides or chelated metals and other therapeutic agents. The therapeutic agents may be linked directly to the antibody or via a carrier such as for example, a liposome, virus or viral particle where the therapeutic agent to be delivered is incorporated as part of the carrier. This technology is well known in the art. Similarly the antibodies of the invention may also be used diagnostically in the identification of areas of inflammation. The antibodies may be unlabelled or may be labelled for example with a radiolabel, e.g. a radionuclide; a chelated metal; a photochemical reagent, e.g. a fluorescent compound; a dye, or a label detectable via reaction with an enzyme, substrate or cofactor, or a compound detected via NMR or ESR spectroscopy.

BRIEF DESCRIPTION OF THE FIGURES

The present invention is now described by way of example only, by reference to the accompanying drawings in which:

FIG. 1a shows the DNA SEQ ID NO:3 and amino acid SEQ ID NO:4 sequence of ENA-2 Vl.

FIG. 1b shows the DNA SEQ ID NO:5 and amino acid SEQ ID NO:6 sequence of ENA-2 Vh.

FIG. 2a shows the DNA SEQ ID NO:7 and amino acid SEQ ID NO:8 sequence of CDR-grafted ENA-2 Vh.

FIG. 2b shows the DNA SEQ ID NO:9 and amino acid SEQ ID NO:10 sequence of CDR-grafted ENA-2 Vl.

FIG. 4a shows a graph of the cell blocking activity of chimeric and mouse ENA-2 antibodies.
- ENA2 1G
- chimeric FIG. 4b shows a graph of the cell blocking activity of CDR-grafted and mouse ENA-2 antibodies.
- ENA2 FAB2
- ENA2 1G
- hENA-2

FIG. 5 shows the sequence SEQ ID NOS:11–22 of mutagenic oligonucleotides.

FIG. 9 is a schematic diagram of the vectors pMRR015 and pMRR011

FIG. 17 shows the results of an experiment to measure complement dependent lysis
1A—Total lysis using 10% SDS.
1B—Medium alone.
1C—Medium+complement.
1D—W6/32+complement.
1E—hENA-2(L235A, S228P)+complement.
1F—hENA 235A)+complement.
2A—W6/32+heat inactivated complement.
2B—hENA-2(L235A, S228P)+heat inactivated complement.
2C—hENA-2(L235A)+heat inactivated complement.
20—hENA-2(L235A)+medium alone.

All error bars are ±1 standard deviation.

Figure 18:
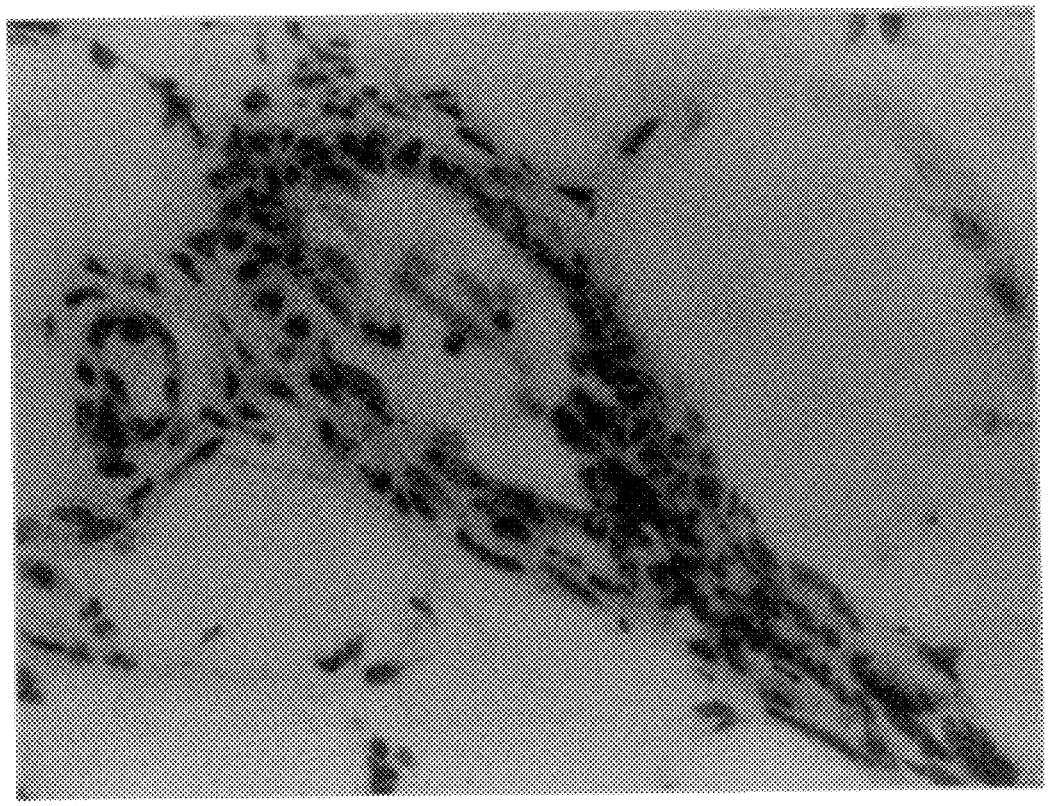
Figure 18:
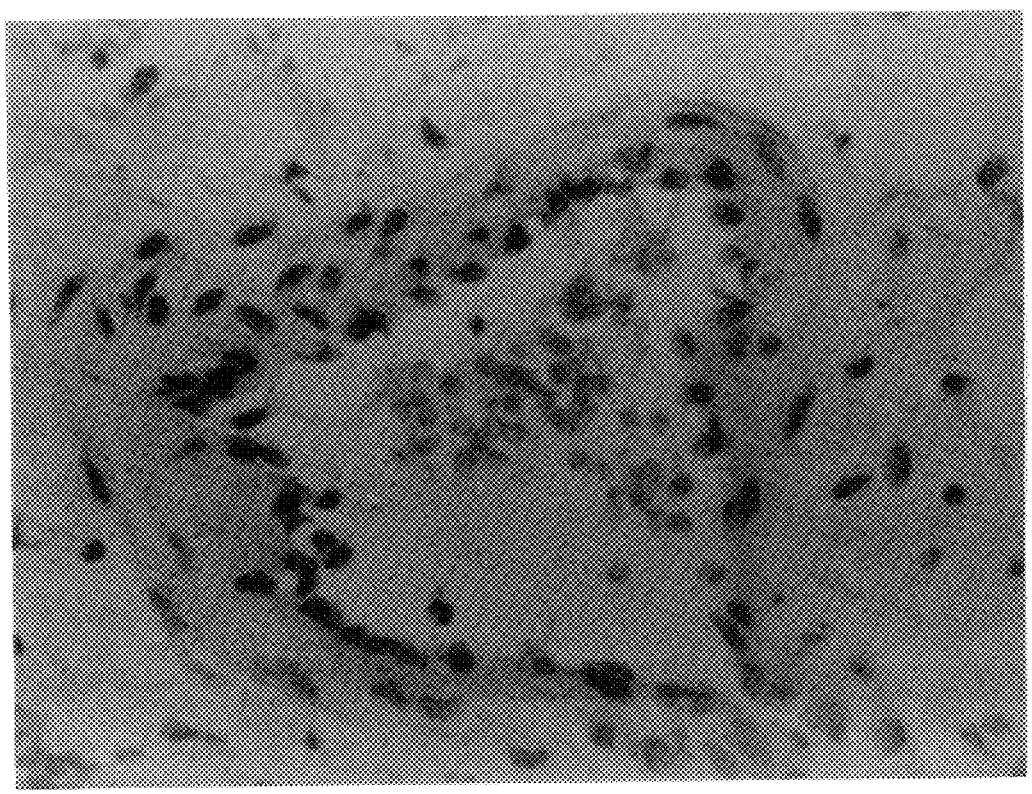

FIG. 18 shows micrographs of haematoxylin and eosin stain sections from biopsies of baboon skin with cytokine induced inflammation
A) saline treated animal
B) hENA-2(L235A) treated animal.

FIG. 19 shows the inhibition of binding of human neutrophils to human E-selectin transfected CHO cells
–□– ENA2 IG
–●– ENA2 FAB2
–◆– Chimeric ENA-2

DESCRIPTION OF SPECIFIC EMBODIMENTS OF THE INVENTION

EXAMPLE 1

Production of Mouse ENA-2 and ENA-2F(ab')2

The hybridoma producing mouse ENA-2 was grown in DMEM medium containing 10% foetal calf serum. Antibody was purified from cell supernatants by affinity chromatography on Protein A-SEPHAROSE. This gel material was used to prepare F(ab')2 fragments by digestion with bromelain followed by Protein A - chromatography to remove the Fc portion and undigested antibody followed by DEAE ion-exchange chromatography to remove the protease.

The first 19 amino acid residues of the ENA-2 light chain were determined by N-terminal protein sequencing.

Cloning mENA-2 Variable Domain Genes and Construction of Chimeric Antibodies

The heavy and light chain variable domains of ENA-2 were cloned using the polymerase chain reaction (PCR). The primers used for the heavy chain were the same as described by Jones and Bendig (1991) (Bio Technology 9 88–89) with minor modifications to enable fragments to be cloned directly into Celltech expression vectors. PCR reactions were carried out using first strand cDNA (PCR conditions 94° 1 min; 55° C. 1 min; 72° C. 1 min for 30 cycles) produced from total RNA by reverse transcriptase. The leader sequence primed product was inserted into pMR014 to produce the chimeric γ4 heavy chain vector pENA202. Four independent heavy chain clones were sequenced and shown to be identical except in the leader sequence as shown in FIG. 1a. The ENA-2 light chain variable domain (Vl) was isolated by PCR using a 5' oligonucleotide primer based on the N-terminal sequence of the murine light chain (FIG. 1b) and a framework 4 3' consensus primer. The PCR product was inserted into the vector pR0102 which contains a light chain leader sequence, thus reconstructing the 5' end of Vl gene. Sequencing of four independent Vl clones only revealed two conservative changes in the DNA sequence (FIG. 1b). The reconstructed Vl gene was inserted into the vector pMR15.1 to produce the chimeric Kappa light chain vector, pEN201.

Design and Assembly of CDR-Grafted ENA-2

The ENA-2 Vh domain showed closest sequence homology to group 1 human heavy chains. Consequently the CDR grafted version of ENA-2 was based on the group 1 human antibody Eu. The design of the CDR-grafted ENA-2 followed the criteria identified in PCT/GB90/02017. The CDRs of both Vh and Vl were defined according to Kabat et al. (1987) (Sequences of proteins of immunological interest 4th edition. Washington DC: United States, Department of Health and Human Services). The CDR sequences in Eu were changed to the corresponding ones of mENA-2. For the CDR grafted Vh, six framework residues were changed to the corresponding residues from mENA-2 at Met 48 lle, Val67 Ala (CDR2 packing residues contacting residue 63) lle 69 Leu, Glu 73 Lys (potential CDR2 contacting residues), Ala93 Thr (Vh/Vl interface residues) and Gly 94 Val (CDR3 packing residue). In addition the following framework residues in Eu were changed to those of the human consensus sequence, Glu103Trp, Tyr104Gly, Asn105Gln and Gly107Thr. The DNA sequence of the CDR-grafted Vh gene is shown in FIG. 2a. In designing the CDR grafted light chain, six changes were made to the Eu framework, Met48lle, Ser60Asp lle63Thr, Glu70Asp, Va111Ile Gly113 Arg. At all these positions the ENA-2 framework residue is more typical of human Vl Antibody sequence than the Eu residue.

The sequence of the CDR-grafted ENA-2 Vl gene is shown in FIG. 2b. The CDR-grafted variable domain genes were assembled by PCR (Daugherty et al (1991) Nucl. Acids Res. 19 2471–2476) using 1pmole of each assembly oligonucleotide (PCR conditions; 94° C. 1 min, 55° C. 1 min, 72° C. 1 min for 30 cycles). CDR grafted Vh and Vl genes were inserted into the vectors pMR011, pMR014 and pMR10.1 to produce the human γ1 heavy chain vector, pENA212, γ4 heavy chain vector pENA206 and the human kappa chain vector pENA204. pMR10.1 is a kappa light chain vector which lacks the Ig/terminator sequence in pMR15.1 (FIG. 9).

Transient Expression of Chimeric and CDR-Grafted ENA-2 Antibodies

Heavy and light chain genes were co-expressed transiently in CHO-L761 cells (Cockett et al, 1991, Nucl. Acids Res. 19 319–325) and cell supernatants assayed for assembled antibody by ELISA.

The assembly ELISA for quantifying antibody yields used microwell plates coated with a goat F(ab')2 anti-human IgGFc. Following incubation with transfected culture supernatants, bound chimeric or CDR-grafted antibody was revealed with a horse radish peroxidase (HRP)-conjugated murine anti-human kappa chain antibody using tetramethyl benzidine (TMB) as the substrate. Concentrations of chimeric or CDR-grafted whole antibody in the samples were interpolated from a calibration curve generated from serial dilutions of purified human IgG4 or IgG1 antibody standards.

Purification and Binding Activity of Chimeric and CDR-Grafted ENA-2 Antibodies

Recombinant antibodies were purified from cell supernatants by affinity chromatography on Protein A-SEPHAROSE. Antigen gel binding activity was compared to ENA-2 in both cell blocking and competition assays. The cell blocking assay was carried out as follows:

Purified Human Polymorphs Were Pre-incubated With Anti-CD18 Antibody and Cooled to 4° C. to Minimise Integrin Binding.

Cells (4×10$^5$ Cells/Well) were Added to CHO Cell Line Transfected with the Gene for Human E-Selectin and Incubated for 60 min at 4° C. in Presence or Absence of Anti-E-Sectin Antibodies.

Cells were Washed to Remove Unbound Cells.

Adherent Cells were Lysed and Endogenous Myeloperoxidase Activity in Polymorphs was Measured in a TMB Assay.

The competition binding assay was carried out as follows. The non-blocking anti-E-selectin 34.27 was coated onto Immunosorp 96 well plates in 0.1M NHCO3 (4° C. overnight at 5 μg/ml). The plate was blocked with 1% BSA (1h, room temperature) and then the Lectin/EGF fragment from E-selectin added at 50 ng/ml (100 μl/ well in PBS room temperature for 1 h). 50 μl of test sample was then added followed by 50 μl of biotinylated murine ENA-2 whole antibody. The assay was left at room temperature for 1 h, streptavidin peroxidase was added and allowed to incubate at room temperature for a further 30 min. Finally, the plate was washed and color developed with the standard TMB reagent.

Figure 3A:
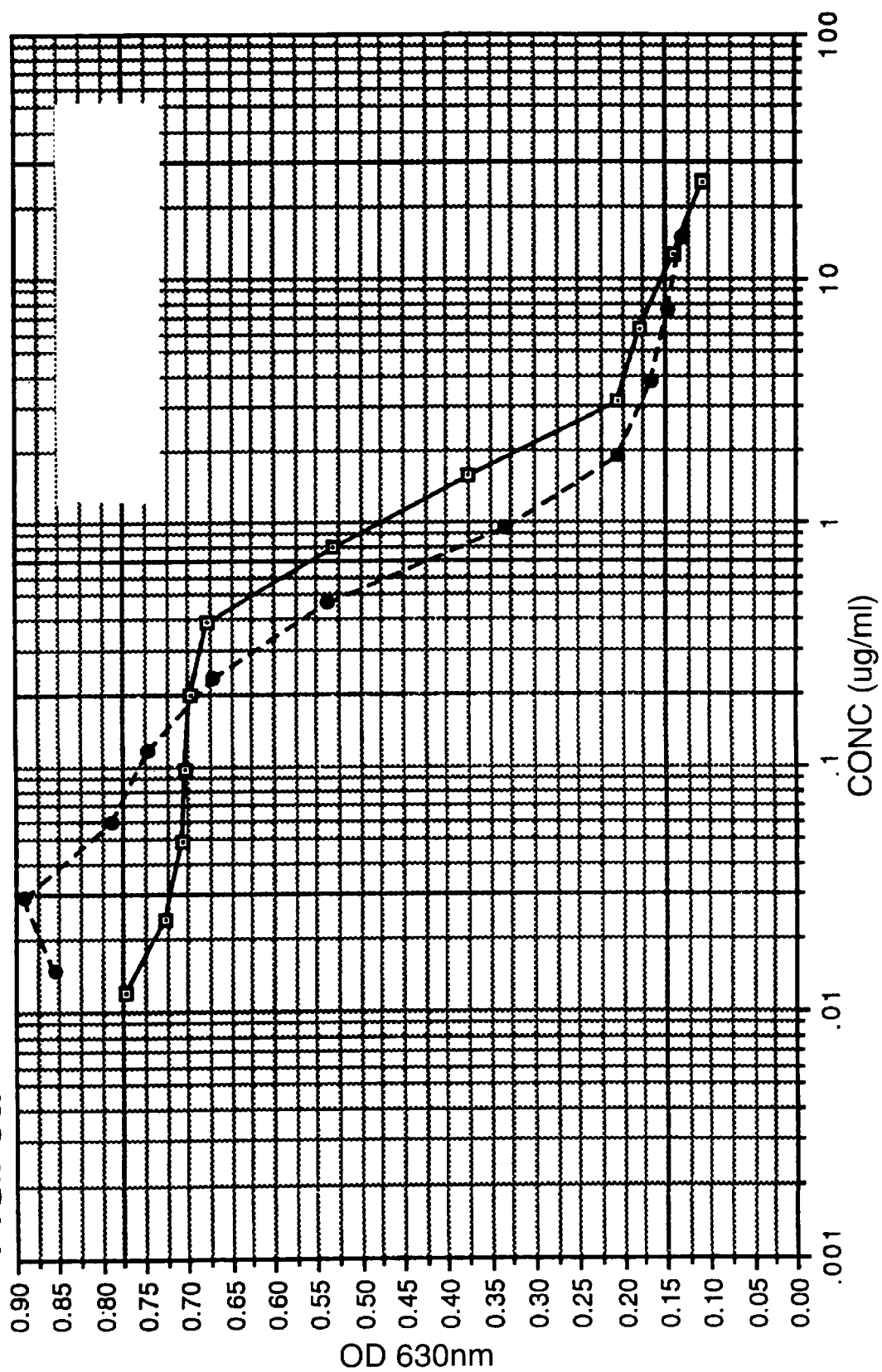
FIG. 3a shows a graph of the competition binding activity of chimeric ENA-2.
- mouse ENA2
- chimeric ENA2
Figure 3B:
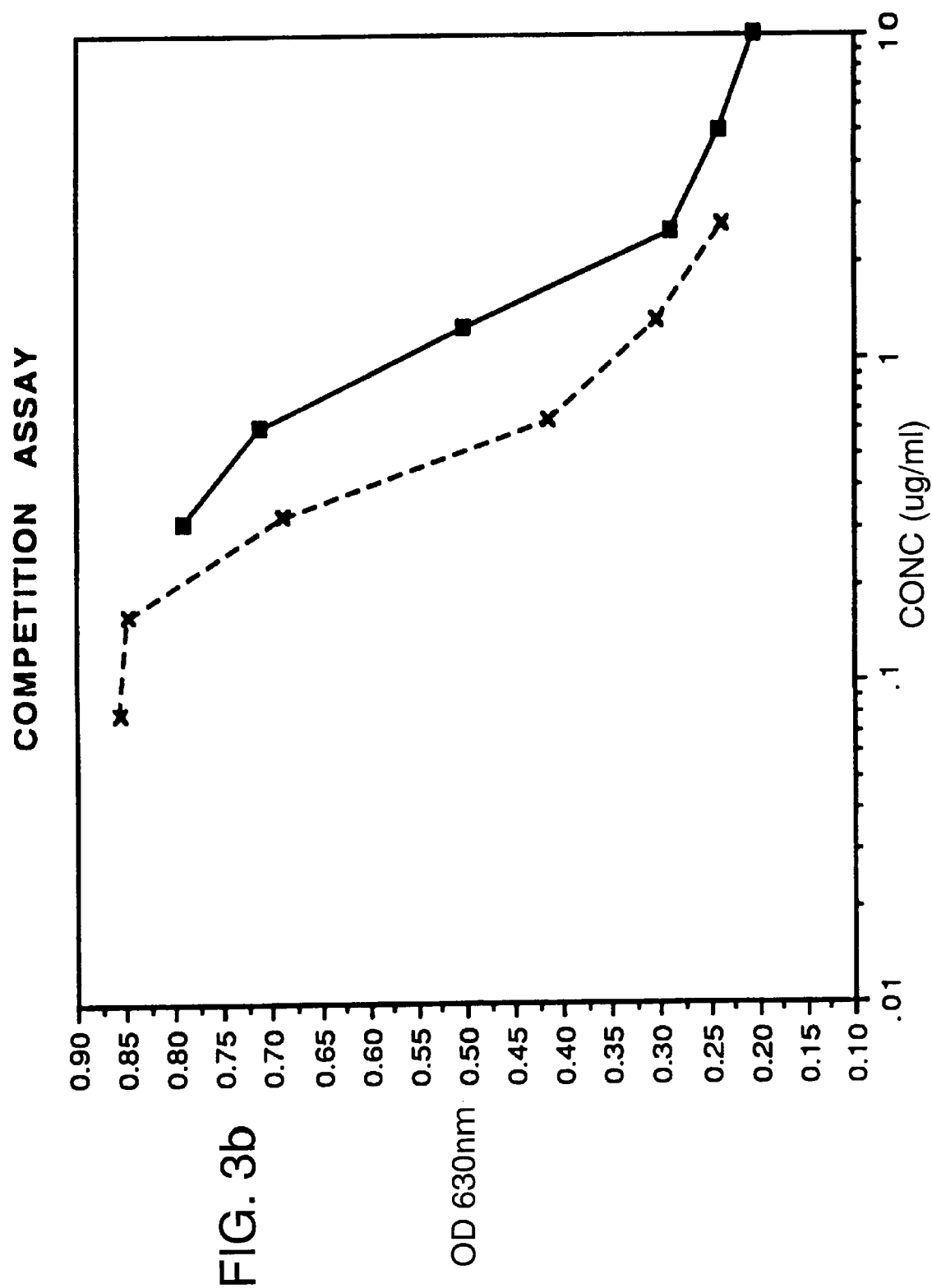
FIG. 3b shows a graph of the competition binding activity of CDR-grafted ENA-2 antibody.
- mouse ENA2
- hENA-2

In both assays chimeric and CDR-grafted ENA-2 showed similar potency to the mouse antibody. Representative data are shown in FIGS. 3 and 4.

The affinity of both mouse and CDR-grafted ENA-2 for E-selectin were measured using a BlAcore TH biosensor (Pharmacia). This instrument combines miniaturised fluid delivery with an optical detection system based on surface plasmon resonance, to monitor protein interactions in real time (Chaiken et al, (1991) Anal. Biochem 201 197–210). The antibodies were immobilised at similar densities onto the sensor surface and the lectin/EGF fragment of E-selectin used as antigen in the fluid phase.

Assays of both antibodies were run at the same time using the same dilutions of antigen. The KD measurements are given below.

| | KD Measurements | |
|---|---|---|
| | KD (Avernge) | Duplicates |
| ENA-2 | 5.43 × 10$^{-9}$M | (5.38 and 5.48) |
| hENA2 | 7.98 × 10$^{-9}$M | (7.8 and 8.17) |

The results indicate that the CDR-grafted ENA-2 retains approximately 70% of the affinity of the mouse antibody.

Construction and Evaluation of Human A Heavy Chain Fc Mutants

Lund et al, 1991 have implicated Leu 235 in the Cγ2 domain of human IgG3 heavy chain in binding of antibody to the high affinity receptor on mononuclear phagocytes (FcRI). Thus changing Leu 235 to Ala or Glu drastically reduces FcRI binding activity (by approx. 90% and 100% respectively). In order to produce a version of human IgG4 lacking FcRI binding activity Leu 235 in the γ4 heavy chain was changed to Ala by the PCR strand overlap procedure (Ho, S. N. et al, 1989), the sequences of the mutagenic oligonucleotides are given in FIG. 5. Ala occurs at position 235 in human γ2 which does not bind to FcRI. This relatively conservative substitution was chosen to minimise the impact of the mutation on the immunogenicity of the IgG4 antibody.

Figure 6:
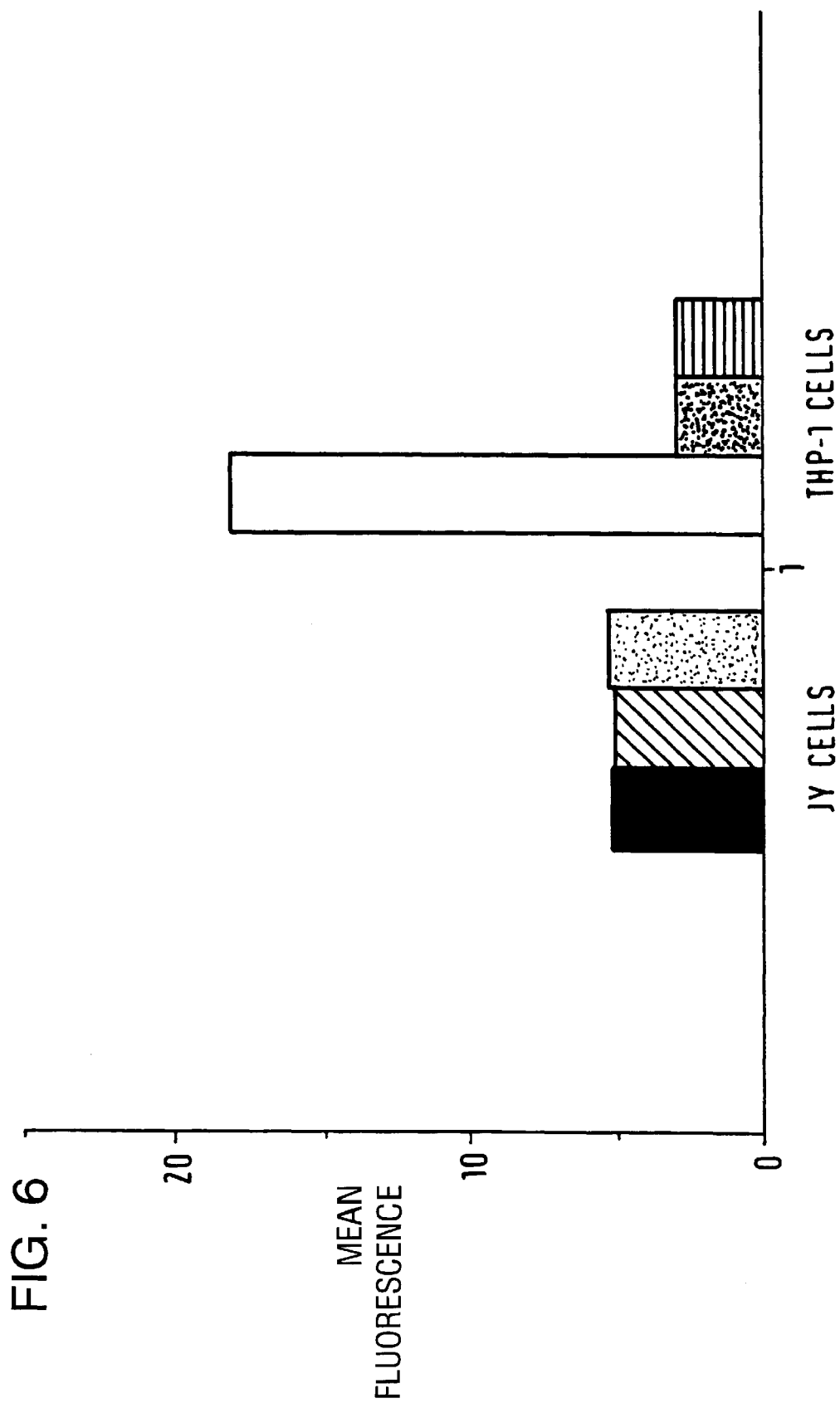
FIG. 6 is a histogram analysis showing the cell binding activity of CDR-grafted hENA-2 (wt) and hENA-2(L235A).
- gamma 4
- no ab
- gamma 4 L235>A
- gamma 4
- no ab
- gamma 4 L235>A

A CDR grafted heavy chain vector containing the L235A mutation (pENA211) was constructed and transiently co-expressed with the CDR-grafted light chain gene in CHO L761 cells. Antibody purified from cell supernatants was evaluated for both antigen-binding and cell binding via FcRI. Competition assays showed that alteration of the Fc had no effect on the antigen-binding activity of the CDR-grafted ENA-2. The binding of hENA-2 to THP1 cells which express FcRI and JY cells which do not, and neither of which express E-selectin, were compared to hENA-2 IgG4 L235A as follows. Cells (5×10$^6$/ml) were incubated for 1 h at room temperature with either hENA-2 wt or hENA-2 L235A antibodies serially diluted in culture medium containing 10% foetal calf serum. The cells were washed with phosphate buffered saline/1% bovine serum albumin, and then incubated with a fluorescein labelled goat anti-(human IgG Fc) antibody for a further 1 h at room temperature. After washing the cells to remove unbound antibody, the binding of FITC labelled antibody to the cells was detected in a FACScan analyser (Becton Dickinson). The results shown in FIG. 6 confirm that the L235A mutation has removed the cell binding activity mediated by FcRI from the hENA-2 antibody.

Figure 7:
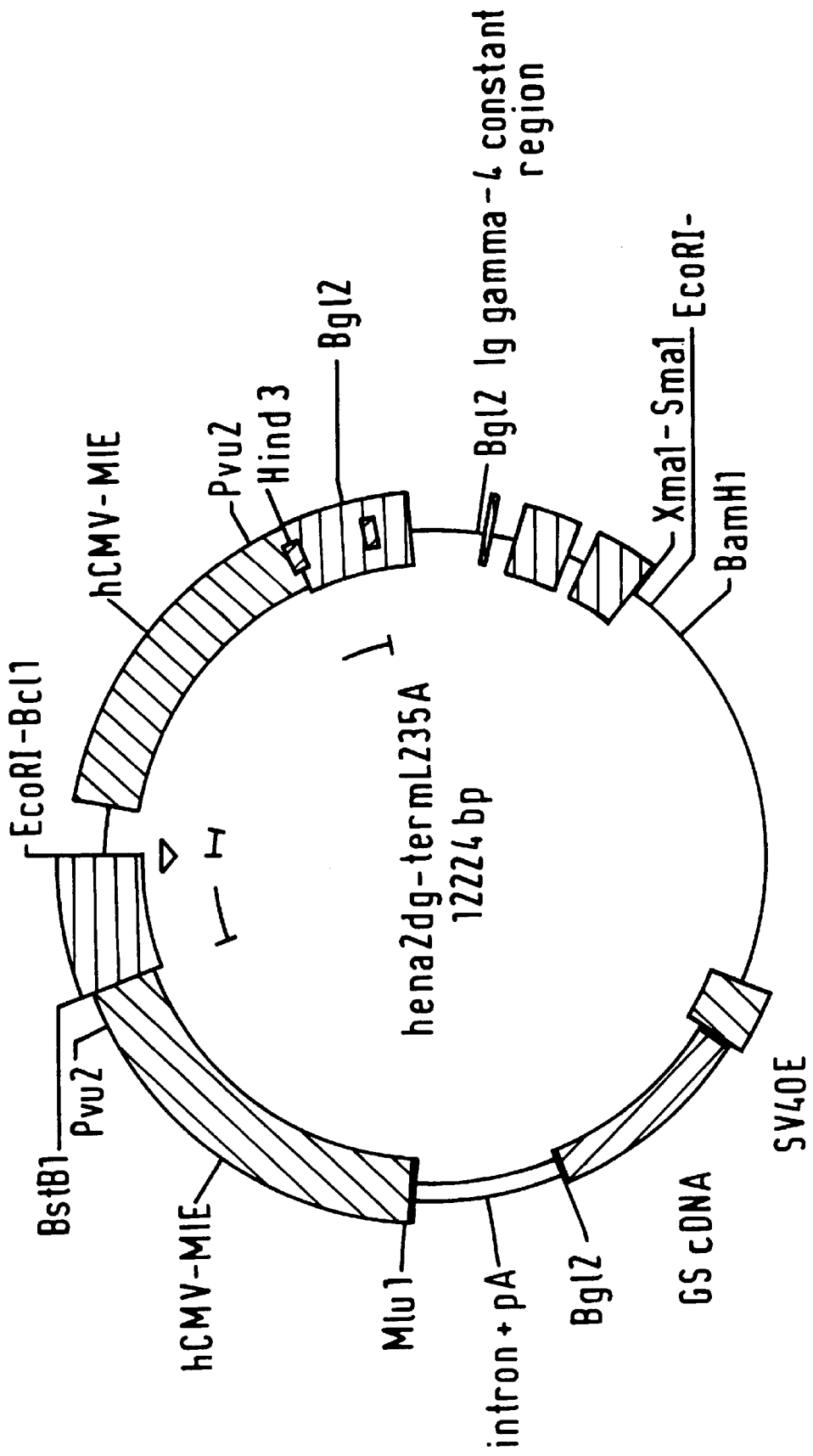
FIG. 7 is a schematic diagram of the expression vector pENA215.
Figure 8:
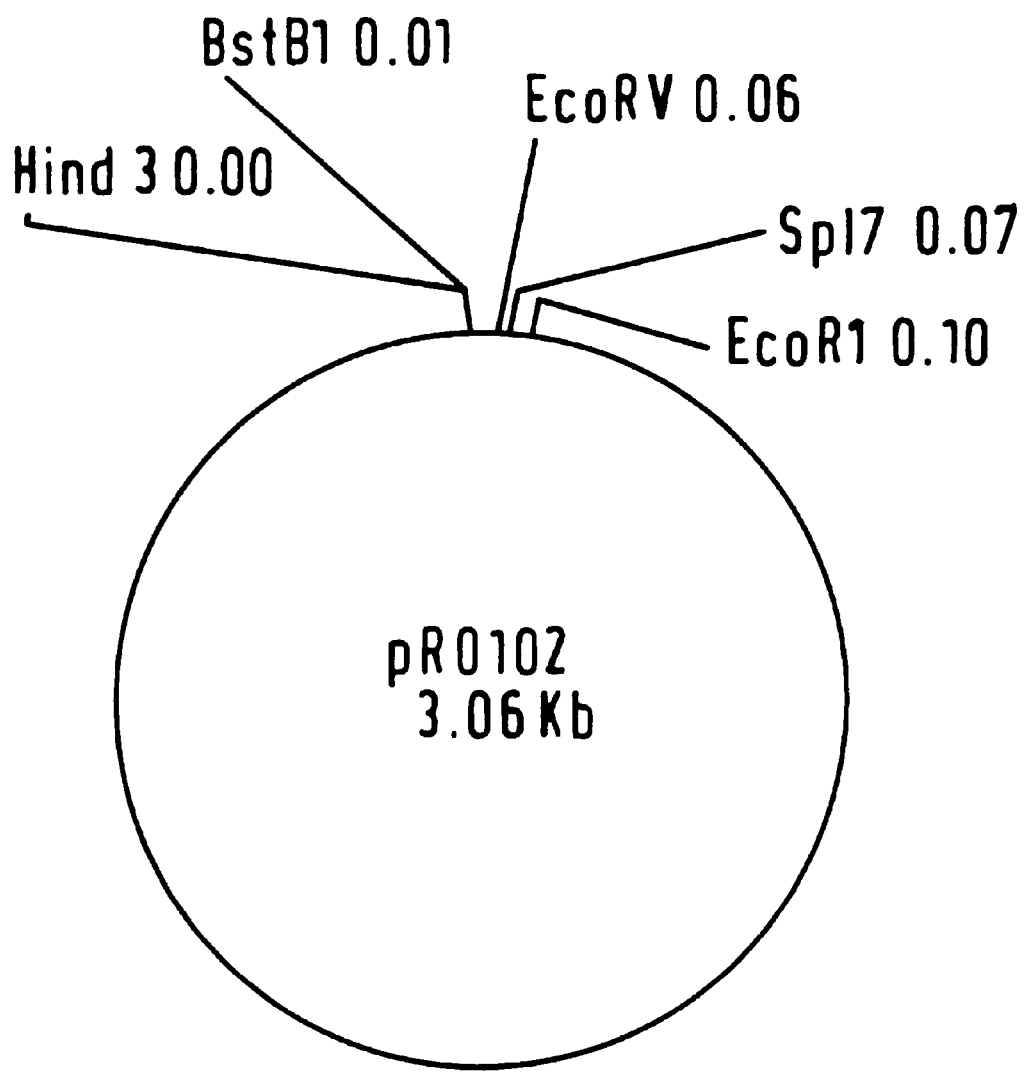
FIG. 8 is a schematic diagram of the expression vector pRO102
Figure 10:
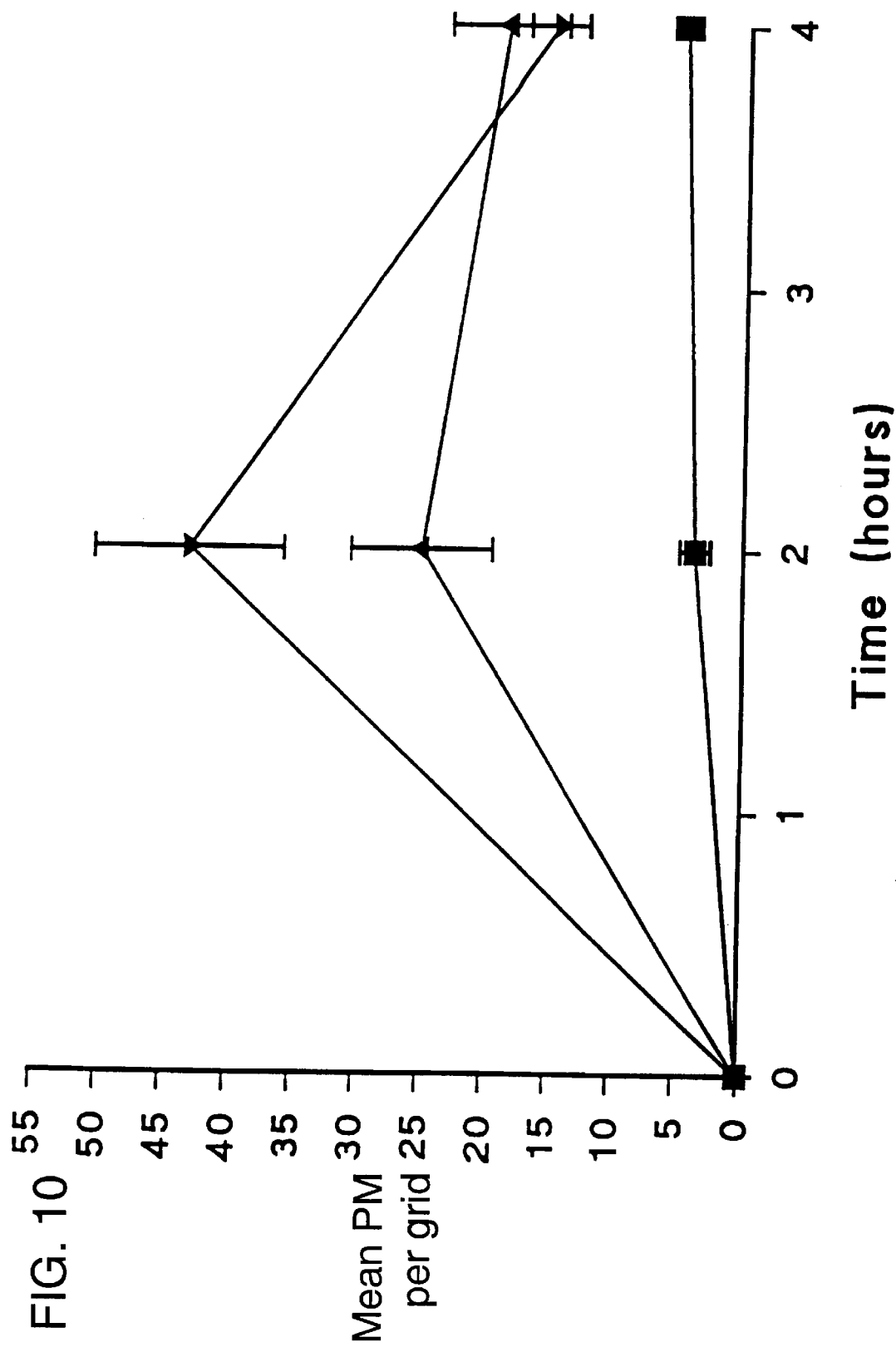
FIG. 10 shows a graph of the effect of hENA-2(L235A) on IL-1 induced PMN infiltration in baboon skin
- saline injected sites (n=12)
- ▲ hENA2(L235A) treated (n=6)
- ▼ saline control treated (n=6)
Figure 11:
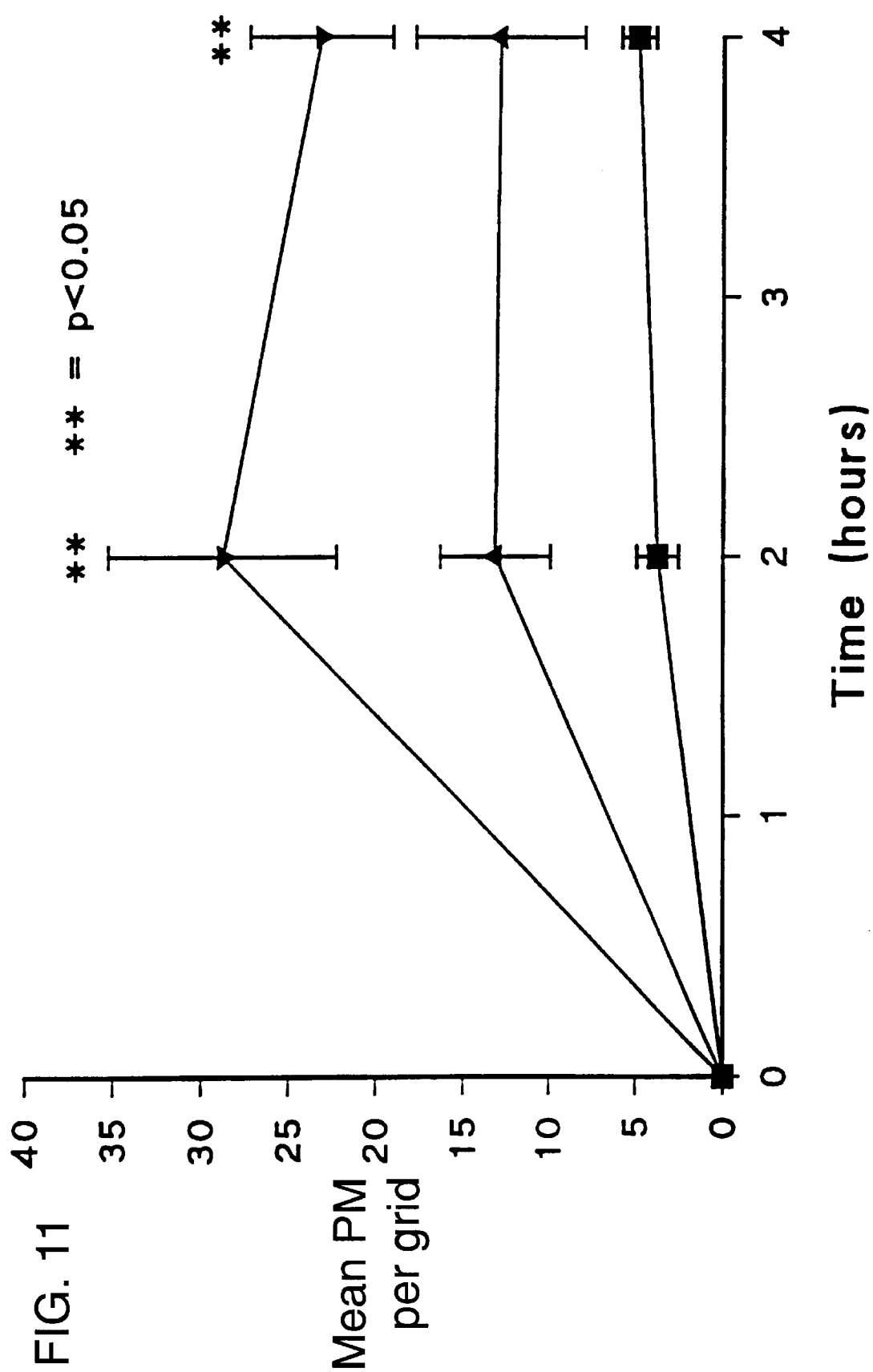
FIG. 11 shows a graph of the effect of hENA-2(L235A) on TNF induced PMN infiltration in baboon skin
■ saline injected sites (n=12)
▲ hENA2(L235A) treated (n=6)
▼ saline control treated (n=6)
P<0.05
Figure 12:
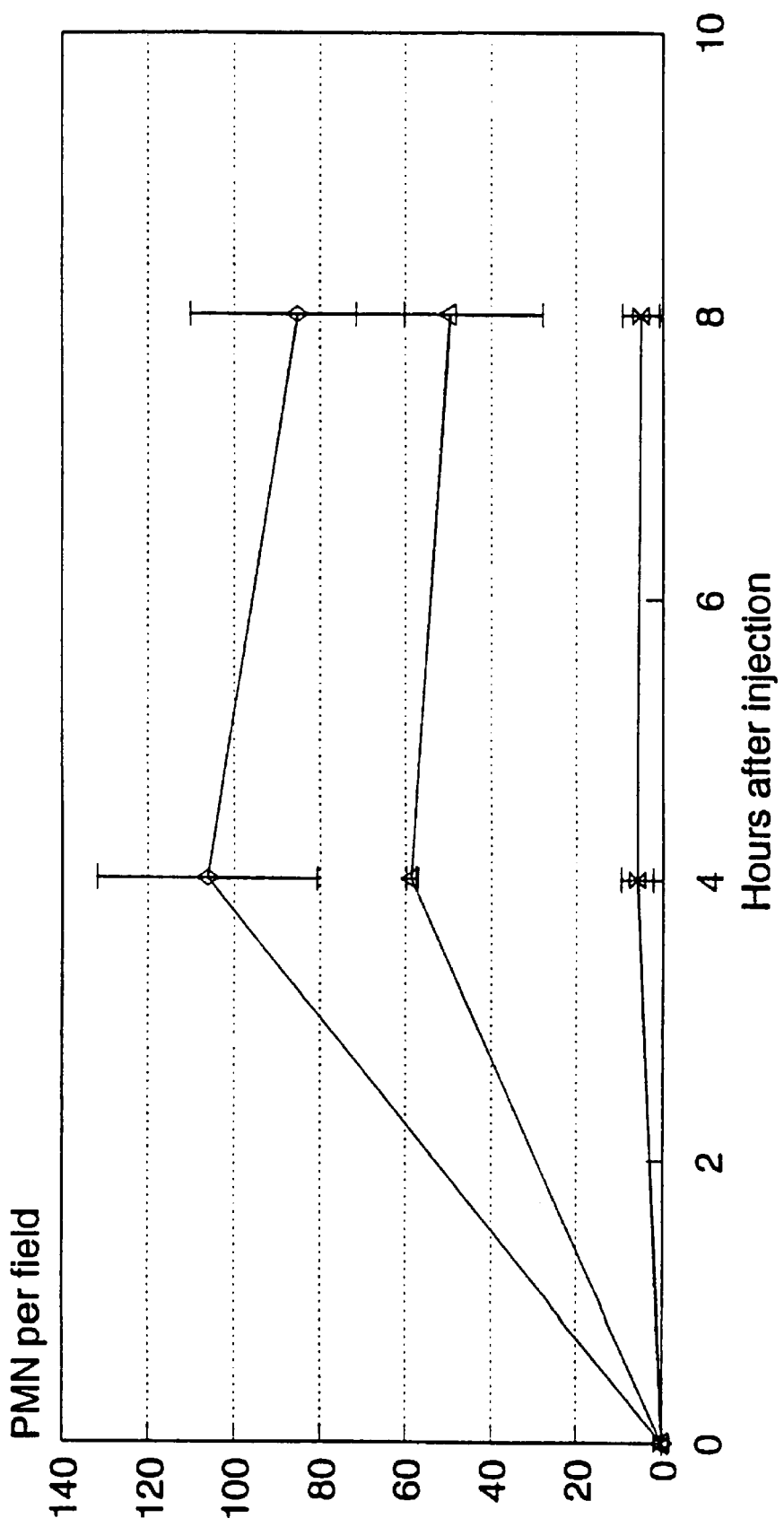
FIG. 12 shows a graph of the effect of ENA-2 (Fab)'$_2$ and controls on PMN in baboon skin after IL-1 induction.
–◇– IL-1 0.1 μg (control)
–△– IL-1 0.1 μg (treated)
–✕– Saline
Figure 13:
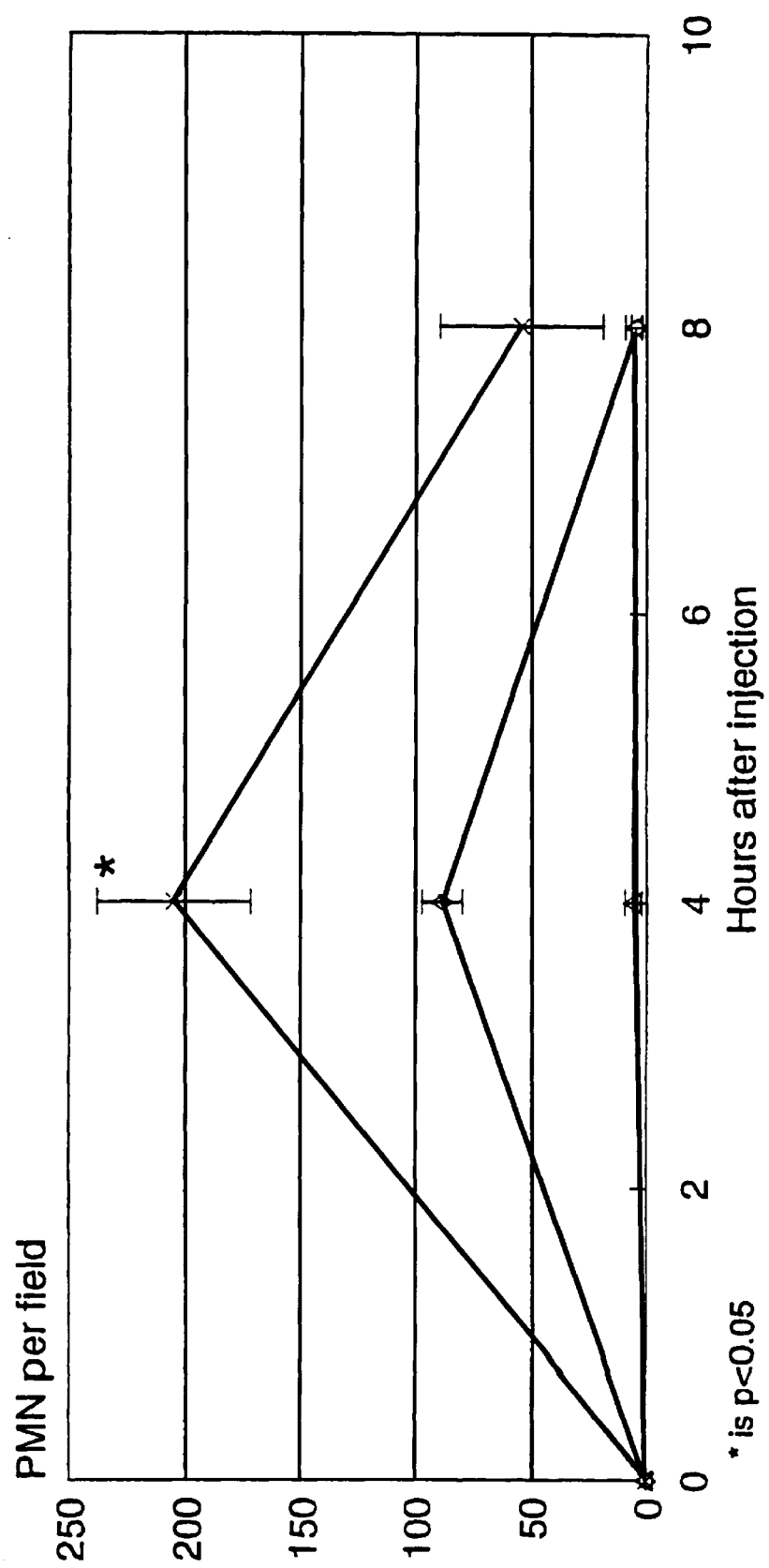
FIG. 13 shows a graph of the effect of ENA-2 (Fab)'$_2$ and controls on PMN in baboon skin after TNF induction
–✕– TNF 5 μg (control)
–◇– TNF 5 μg (treated)
–△– Saline combined
P<0.05

Expression of CDR-grafted ENA-2 Antibodies in NSO Cells hENA-2 (L235A) was expressed in NSO cells to produce sufficient quantities of antibody for functional characterisation in animal models. Cell lines were established using the glutamine synthetase selectable marker (See published International Patent No. WO 87/04462). A double gene expression vector was constructed by inserting the CDR grafted heavy chain gene on a Not-Bam restriction fragment into the CDR-grafted light chain vector pENA204 to produce plasmid pENA215 (FIG. 7). NSO cells were transfected by electroporation and cell lines producing recombinant antibody selected using glutamine free media.

Construction and Expression of Human γ4 Hinge Mutant (S228P)

Angal et al (1993) Molecular Immunol. 30, 105–108, have shown that changing Ser 228 in the hinge of a human γ4 chimeric antibody abolishes the formation of half antibody molecules which is a property of natural IgG4 antibodies. Therefore to reduce the heterogeneity of the hENA-2 L235A antibody the S228P change was introduced into the molecule. Mutagenesis was carried by the PCR strand overlap procedure (HO SN et al, 1989) using the following primers:
R5989
5' CCA TGC CCA TGC CCA GGT AAG CC 3' SEQ ID NO:1
R5990
5' CCT GGG CAT GGT GGG CAT GGG GGA CC 3' SEQ ID NO:2

The resulting CDR-grafted heavy chain was combined with the CDR-grafted light chain in a double gene vector for transfection into NSO cells. Cell lines were established producing the hENA-2 L235A, S228P antibody with yields of approximately 400 mg/L in suspension culture. The antigen-binding properties of this antibody were indistinguishable from the hENA-2-wt and hENA-2 L235A antibodies. However, the formation of half antibody molecules was reduced from ~10% to less than 1% as judged by SDS PAGE analysis of purified protein.

CDR-grafted hENA-2 heavy chain vector =pENA216 and double gene expression vector =pENA217 (see FIG. 7).

Figure 16:
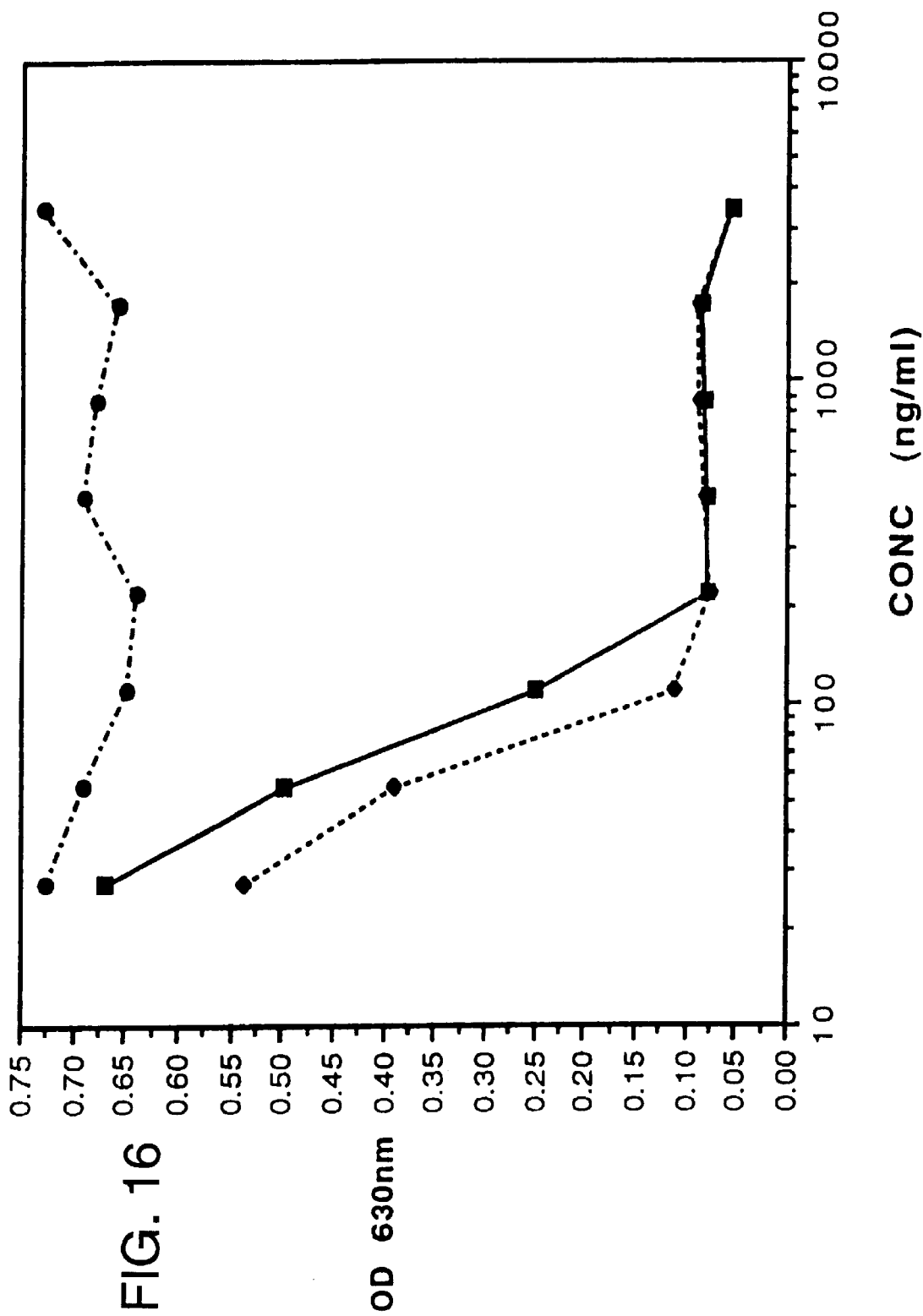
FIG. 16 shows the effect of
hENA-2(L235A)–■–
hENA-2(L235A, S228P)–●–
MOPC 21 –◆– on the binding of human PMN to E-selectin transfected CHO cells.

FIG. 16 shows the effects of hENA-2 (L235A) and the above derivative of hENA-2 (L235A, S228P) on the binding of human PMN to E-selectin transfected CHO cells. The method was as described previously on pages 19 to 20. MOPC-21 is used as a negative control antibody.

EXAMPLE 2

We have investigated the effects of ENA-2 F(ab)'$_2$ and the fully engineered human variant, hENA-2 (L235A), in cytokine induced inflammation in baboons.

Intradermal injections of recombinant human IL-1 α (rhIL-1), 0.1 and 1.0 µg/site, and recombinant human TNF α(rhTNF), 5 µg/site, were made in adult baboons. Injections were made, to a pre-determined random grid pattern, at 2, 4 or 8 hours prior to taking full thickness skin biopsies with an 8 mm diameter skin biopsy punch. Each mediator was given as a 0.1 ml injection in triplicate sites at two time points. Light general anaesthesia was used for the biopsies. The tissues were processed for either formalin fixed paraffin wax histology with haematoxylin and eosin staining or chilled to −70° C. for cryostat sectioning and immunohistochemical analysis. Blood samples were taken to determine if the treatment had any effect on circulating blood cells and for antibody pharmacodynamic analysis. Control animals received an equal volume of intravenous saline.

Injection of rhIL-1 and rhTNF caused an up regulation of E-selectin as detected immunohistochemically and a predominantly neutrophil cellular infiltrate into the deep dermis. Treatment with ENA-2 F(ab)'$_2$ (5 mg/kg iv). prior to the cytokine injections attenuated the cellular response at both 4 and 8 hours. This reduction was significant at the 4 hour time point in the TNF injected sites (57% p<0.05). In a second experiment using the engineered human antibody hENA-2 (L235A) (3.0 mg/kg iv) there was again a good reduction in cellular inflammation which was significant at 2 and 4 hours for the TNF injected sites (54% and 45% respectively p<0.05). The degree of inflammation in the IL-1 injected sites was reduced in both the ENA-2 and hENA-2(L235A) treated animals but this did not reach statistical significance. No effect was seen with either antibody on circulating cells.

The results are shown in FIGS. 10 to 13.

Figure 14:
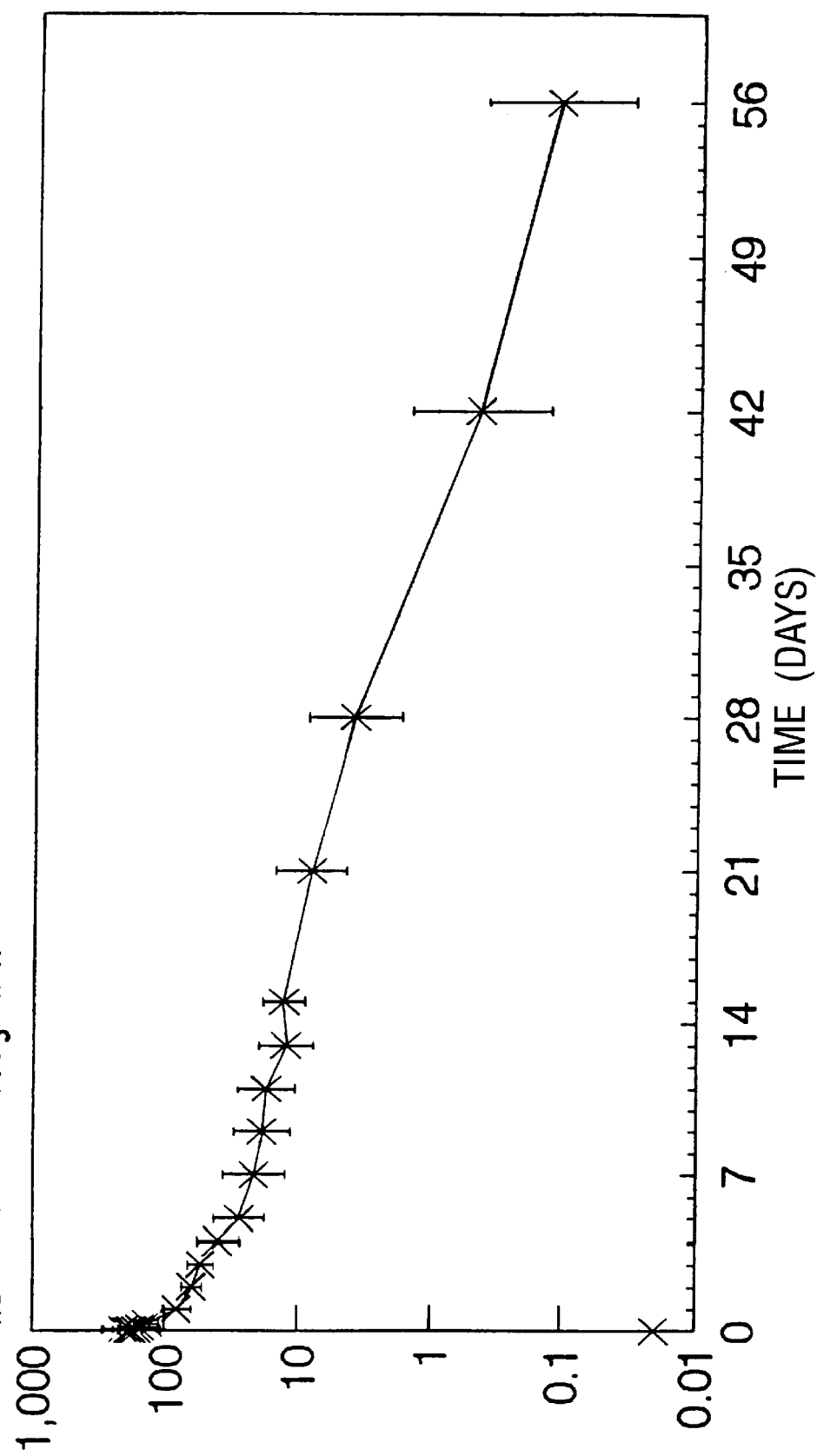
FIG. 14 shows a graph of circulating hENA-2(L235A) levels in the animals used in FIGS. 12 and 13 as measured by a cell-based assay system.
Figure 15:
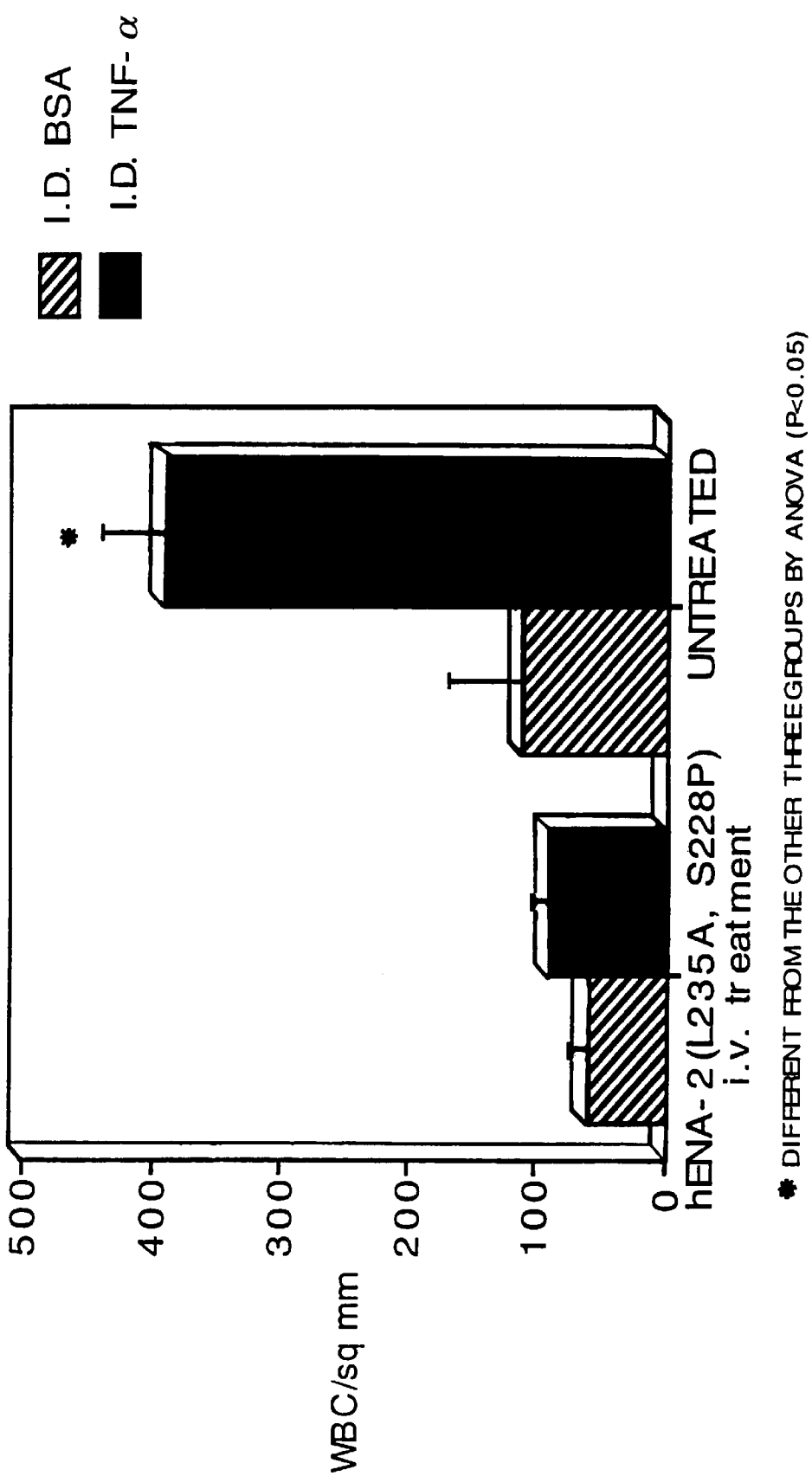
FIG. 15 shows a graph of white blood cell trafficking in human skin xenografts on SCID mice after intradermal challenge with:
BSA ■
TNF ■ and i.v. treatment with hENA-2(L235A, S228P).

This shows that a whole antibody of neutral isotype can be used to inhibit leukocyte extravasation at inflammatory sites. This antibody had a long circulating half-life and could still be detected in the circulation 56 days after treatment (FIG. 14) measured as described below.

hENA2(L235A) CELL-BASED ASSAY

AIM

To measure levels of hENA2(L235A) in baboon plasma samples, in order to investigate the Ab's pharmacokinetics.

PRINCIPLE

E-selectin-transfected CHO cells are grown on 96-well tissue culture plates. hENA2(L235A) in baboon plasma binds to E-selectin expressed on cell surfaces and is revealed with a murine anti-human IgG4-HRP & TMB.

REAGENTS

Falcon Microtest III Tissue Culture Plates

E-selectin-transfected CHO's

CB2 DMEM Base+10% Dialysed FCS (tissue culture medium)

Murine anti-human IgG4-HRP, Serotec MCA517P.

Dulbecco's PBS

PBS/1%BSA.

NMS, Serotec C11SB.

TMB substrate.

STANDARD & IAC PREPARATION

STANDARD CURVE:

hENA2 diluted to give top standard of 250 ng/ml. Doubling dilutions in 1% BSA/PBS to give 125, 62.5, 31.25, 15.6, 7.8 and 3.9 ng/ml (plus zero). Stored in 0.5 ml aliquots at −70° C.

IAC's

Controls made up to 60, 25 and 7.5 ng/ml hENA2 (L235A) in 1% BSA/PBS.

Stored in 0.5 ml aliquots at −70° C.

SAMPLE PREPARATION:

Samples diluted in 1% BSA/PBS at a range of dilutions, from 1:10,000 down to 1:10, as for the ELISA.

PROTOCOL:

1. CHO's were plated out into tissue culture plates at $10^5$/ml in tissue culture medium (100 µl/well), using only the middle 60 wells of each plate.

2. Cells were allowed to grow to confluence for 48 hours before assaying, until a monolayer was obtained.

3. Medium was removed with a multichannel pipette and cells were washed once with 100 µl/well PBS (again using a multichannel).

4. Cells were blocked with 1% BSA/PBS, 30 mins, RT, shaking.

5. Plate washed×2 100 µl/well PBS (with multichannel).

6. 50 µl/well 1% BSA/2% NMS/PBS was added.
7. 50 µl/well standard/IAC/sample, added as appropriate.
8. Plate incubated 1 h, RT, shaking gently. Washed×2 PBS.
9. MαHuIgG4-HRP diluted at 1:2000, 100 µl/well added.
10. Incubated 30 mins, RT, shaking gently. Washed×2 PBS as before.
11. 100 µl TMB substrate/well added and absorbance read at 630 nm.

N.B. A multichannel pipette was used to wash the cells and to add each reagent, the plates were shaken gently, they were not tap-dried, and there were only 2 washes with PBS at each stage. These precautions were taken to avoid cells being removed from the plate.

EXAMPLE 3

The engineered human anti-E-selectin antibody, the production of which is described in Example 1 (ie hENA-2, L235A,S228P$_{\gamma 4}$ isotype) recognises human E-selectin and, under appropriate conditions, prevents PMN adhesion to activated endothelial cells. In order to confirm that the antibody could inhibit the migration of leukocytes into human skin in an in vivo setting a model using human skin grafted onto SCID mice has been utilised. This model was first reported by Yan et al (J. Clin Invest. 91 986–996 (1993)) and has subsequently been used to show that a murine anti-human E-selectin antibody can inhibit leukocyte trafficking Yan et al (J. Immunol 152 3053 (1994)). In this model mouse leukocytes (predominantly PMN) migrate into the human skin via human endothelial cells in response to injected cytokine.

METHOD

After anaesthesia, 6–8 week old SCID mice (purchased from Wistar Institute) were prepared for transplantation by shaving the hair from a 5 cm$^2$ area on each side of the lateral abdominal region. Two circular graft beds approximately 1.5 cm in diameter were created on the shaved areas by removing full thickness skin down to the fascia. Full thickness human skin grafts were placed onto the wound beds and held in place with 6–0 non-absorbable monofilament suture material. The human skin consisted of neonatal foreskins from elective circumcisions or normal adult skin removed during plastic surgery. Each experimental mouse received an intravenous injection of 50 µg of anti-E-selectin Ab in saline. Control animals received no intravenous injection. The graft on the left side of each animal was then injected with 50 µl of normal saline containing a small amount of BSA and colloidal carbon to identify the injection site. The right graft was injected with 6000 units of human recombinant TNFα in 50µl of normal saline containing a small amount of colloidal carbon. After 4 hours the animals were killed and skin sections removed and stored in liquid nitrogen. Immunohistology was performed using standard techniques and sections stained with anti-murine Mac-1, anti-human PECAM-1 and anti-human ICAM-1. This allowed identification of infiltrating murine PMD and confirmed the presence of human endothelial cells lining the blood vessels in the human tissue. The ICAM staining was used as a control to determine that an inflammatory response had been stimulated by the injected TNF. Animals not showing upregulated ICAM-1 expression on basal keratinocytes following TNF injection were excluded from the study. As a further control the saline injected grafts were examined for infiltrating leukocytes. A percentage of animals show high levels of infiltrating leukocytes even in the absence of cytokine injection. This may indicate an ongoing rejection of the graft. Animals showing greater than 100 leukocytes/mm$^2$ in the saline injected graft were excluded from the study.

Multiple sections (four to six) were cut from the centre of each skin biopsy and three to six randomly chosen ×100 microscope fields were examined and the number of infiltrating leukocytes counted.

A total of 14 animals were included in the study but 4 were excluded because the TNF injection site in these animals showed no ICAM-1 upregulation on basal keratinocytes at the TNF injection site. A further animal was excluded from the study because of high levels of infiltration leukocytes in the saline injected graft. Four animals received 50 µg of anti-E-selectin Ab. Four animals received no i.v. treatment.

EXAMPLE 4 hENA-2(L235A, S228P)—Complement Dependent Lysis

Method

Human dermal microvascular endothelial cells, (HMVECS), (Clonetics) were plated at 5×10$^3$ cells per well into 96 well microtitre plates and cultured in Endothelial Growth medium, (EGM), (Clonetics). 5 Days after plating the cells were labelled with 50 Kbq per well $^{51}$Chromium overnight at 37° C. The cells were then washed in EGM and treated with human TNFα, (R & D Systems), at 20 ng/ml in EGM for 6 h at 37° C. to upregulate E-Selectin.

The plates were washed 5 times in Dulbecco's modified eagle's medium, (DMEM), containing 1% FCS.

Test samples were then added to the appropriate wells. The monoclonal antibodies, (W6/32, mouse anti-human Class I; hENA-2(L235A) and hENA-2(L235A, S228P) anti-human E-selectin), were added to give a final concentration of 10 µg/ml in DMEM+1%FCS. Rabbit complement (reconstituted according to manufacturer's recommendation) was added to give a final concentration of 12.5% in DMEM+1% FCS. Where appropriate the complement was heat inactivated at 56° C. for 35 min. Maximum lysis was determined by adding 10% sodium dodecyl sulphate, (SDS). After 1 h 100 µl supernatant was harvested from each well and $^{51}$Chromium release in CPM determined on a gamma counter. Results were averages of six replicates. The results are shown in FIG. 17.

RESULT

Neither hENA-2(L235A S228P) nor hENA-2(L235A) mediate complement dependent lysis of human microvascular endothelial cells under conditions whereas the mouse monoclonal antibody W6/32 causes lysis.

EXAMPLE 5

An experiment was carried out to determine the effect of hENA-2(L235A) on endothelial cell integrity. The results are presented in FIG. 18 which shows micrographs (×1890) of haemotoxylin and eosin stained sections from biopsies of baboon skin with cytokine (TNF-α, 5.0 µg; 2 hr) induced inflammation. Upper micrograph shows endothelium from a saline treated animal with associated PMN infiltrate whilst the lower micrograph shows endothelium from a hENA-2 (L235A) (3 mg/kg) treated animal with only one or two associated PMNs. No discernible difference in endothelium integrity can be seen between the two treatments.

EXAMPLE 6

FIG. 19 shows the inhibition of binding of human neutrophils to human E-selectin transfected CHO cells. The experiment was performed as described in Example 1. The figure shows the effects of different versions of ENA-2 on neutrophil binding from a donor with Fc receptors that interact with many isotypes. The binding is only partly inhibited by the whole murine parent (ENA-2 IG) which is a murine γ1 antibody. The binding can be inhibited by F(ab')₂ of the same antibody showing that most of the binding is caused by an Fc interaction. The chimeric ENA-2 antibody is a full length antibody with the Fc region found in hENA-2. This clearly does not interact with the Fc receptors of this donor and blocks nearly as well as the F(ab')₂ fragment.

What is claimed is:

1. An antibody having specificity for E-selectin characterised in that the serine residue at position 228 of the hinge region has been altered to a proline residue.

2. An antibody according to claim 1 wherein said antibody is an engineered human antibody.

3. An antibody according to claim 2 wherein said antibody has an antigen binding site wherein at least one of the complementarity determining regions of the variable domain is derived from a non-human monoclonal antibody and the remaining immunoglobulin derived parts of the engineered human antibody molecule are derived from a human immunoglobulin.

4. An antibody according to claim 3 wherein said non-human antibody is ENA-2.

5. An antibody according to claim 1 which recognizes the lectin or EGF domain of E-selectin.

6. An antibody according to claim 5 which blocks greater than 80% of human neutrophil binding to E-selectin in an in vitro assay.

7. An antibody according to claim 5 or 6 which is hENA-2(L235A, S228P).

8. A process for the production of an antibody having specificity for E-selectin characterised in that the serine residue at position 228 of the hinge region has been altered to a proline residue which process comprises:
  a) producing in an expression vector an operon having a DNA sequence which encodes an antibody heavy or light chain;
  b) producing in an expression vector an operon having a DNA sequence which encodes a complementary antibody heavy or light chain;
  c) transfecting a host cell with both operons; and
  d) culturing the transfected cell line to produce the antibody.

9. A process according to claim 8 wherein one of said operons has a DNA sequence which encodes an antibody heavy or light chain comprising a variable domain wherein at least one of the CDRs of the variable domain is derived from a non-human immunoglobulin and the remaining immunoglobulin derived parts of the antibody chain are derived from a human immunoglobulin and said other operon has a DNA sequence which encodes a complementary antibody light or heavy chain comprising a variable domain wherein at last one of the CDRs of the variable domain is derived from a non-human immunoglobulin and the remaining immunoglobulin derived parts of the antibody chain are derived from a human immunoglobulin.

10. A process according to claim 9 wherein at least one of the operons has a DNA sequence encoding an antibody heavy chain wherein one or more amino acid residues in the Fc region of said antibody has been altered from that in the naturally occurring sequence.

11. A process according to claim 10 wherein at least one of the operons has a DNA sequence encoding an antibody heavy chain wherein one or more amino acid residues in the Fc region of said antibody including residue 235 in the CH2 domain has been altered from that in the naturally occurring sequence.

12. An antibody having a heavy chain comprising the sequence of SEQ ID NO:8.

13. An antibody having a light chain comprising the sequence of SEQ ID NO:10.

* * * * *

UNITED STATES PATENT AND TRADEMARK OFFICE
CERTIFICATE OF CORRECTION

PATENT NO.    : 6,204,007 B1                                          Page 1 of 1
DATED         : March 20, 2001
INVENTOR(S)   : Owens et al.

It is certified that error appears in the above-identified patent and that said Letters Patent is hereby corrected as shown below:

Column 10,
Line 1, please insert -- The -- before the word "therapeutic";

Column 13,
Line 34, please delete "A-SEPHAROSE" and insert therefor -- A-SEPHAROSE gel --;

Column 14,
Line 14, "(In KD Measurements Table) please delete "KD Avernge" and insert therefor -- KD Average -- ;
Line 22, please delete "A" and insert therefor -- $\gamma 4$ --;

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "PCR primer R5989 (page 26)"

(xi) SEQUENCE DESCRIPTION: SEQ ID NO: 1:

CCATGCCCAT GCCCAGGTAA GCC                                           23

(2) INFORMATION FOR SEQ ID NO: 2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "PCR primer R5990 (page 26)"

(xi) SEQUENCE DESCRIPTION: SEQ ID NO: 2:

CCTGGGCATG GTGGGCATGG GGGACC                                    26

(2) INFORMATION FOR SEQ ID NO: 3:

(i) SEQUENCE CHARACTERISTICS:
      (A) LENGTH: 402 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 3:

ATGAGTGTGC CCACTCAGGT CCTGGGGTTG CTGCTGCTGT GGCTTACAGA TGCCAGATGT    60

GATATCGTGA TGACCCAGTC TCCCTCCTCC CTGACTGTGA CAGCAGGAGA GAAGGTCACT   120

ATGCGCTGCA AGTCCAGTCA GAGTCTGTTA AACAGTGGAA ATCAACAGAA CTACTTGACC   180

TGGTACCAGC AGAAACCAGG GCAGCCTCCT AAACTTTTGA TCTATTGGGC ATCCACTAGG   240

GAATCTGGGG TCCCTGATCG CTTCACAGGC AGTGGATCTG GAACAGATTT CACTCTCACC   300

ATCAGCAGTG TGCAGACTGA AGACCTGGCA GTTTATTACT GTCAGAATGA TTATGATTAT   360

CCGCTCACGT TCGGTGCTGG CACCAAGCTG GAGATCAAAC GT                   402

(2) INFORMATION FOR SEQ ID NO: 4:

(i) SEQUENCE CHARACTERISTICS:
      (A) LENGTH: 134 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 4:

| Met | Ser | Val | Pro | Thr | Gln | Val | Leu | Gly | Leu | Leu | Leu | Leu | Trp | Leu | Thr |
|---|---|---|---|---|---|---|---|---|---|---|---|---|---|---|---|
| 1 | | | | 5 | | | | | 10 | | | | | 15 | |

| Asp | Ala | Arg | Cys | Asp | Ile | Val | Met | Thr | Gln | Ser | Pro | Ser | Ser | Leu | Thr |
|---|---|---|---|---|---|---|---|---|---|---|---|---|---|---|---|
| | | | 20 | | | | | 25 | | | | | 30 | | |

| Val | Thr | Ala | Gly | Glu | Lys | Val | Thr | Met | Arg | Cys | Lys | Ser | Ser | Gln | Ser |
|---|---|---|---|---|---|---|---|---|---|---|---|---|---|---|---|
| | | 35 | | | | | 40 | | | | | 45 | | | |

| Leu | Leu | Asn | Ser | Gly | Asn | Gln | Gln | Asn | Tyr | Leu | Thr | Trp | Tyr | Gln | Gln |
|---|---|---|---|---|---|---|---|---|---|---|---|---|---|---|---|
| | 50 | | | | | 55 | | | | | 60 | | | | |

| Lys | Pro | Gly | Gln | Pro | Pro | Lys | Leu | Leu | Ile | Tyr | Trp | Ala | Ser | Thr | Arg |
|---|---|---|---|---|---|---|---|---|---|---|---|---|---|---|---|
| 65 | | | | | 70 | | | | | 75 | | | | | 80 |

| Glu | Ser | Gly | Val | Pro | Asp | Arg | Phe | Thr | Gly | Ser | Gly | Ser | Gly | Thr | Asp |
|---|---|---|---|---|---|---|---|---|---|---|---|---|---|---|---|
| | | | | 85 | | | | | 90 | | | | | 95 | |

| Phe | Thr | Leu | Thr | Ile | Ser | Ser | Val | Gln | Thr | Glu | Asp | Leu | Ala | Val | Tyr |
|---|---|---|---|---|---|---|---|---|---|---|---|---|---|---|---|
| | | | 100 | | | | | 105 | | | | | 110 | | |

| Tyr | Cys | Gln | Asn | Asp | Tyr | Asp | Tyr | Pro | Leu | Thr | Phe | Gly | Ala | Gly | Thr |
|---|---|---|---|---|---|---|---|---|---|---|---|---|---|---|---|
| | | 115 | | | | | 120 | | | | | 125 | | | |

| Lys | Leu | Glu | Ile | Lys | Arg |
|---|---|---|---|---|---|
| | 130 | | | | |

(2) INFORMATION FOR SEQ ID NO: 5:

(i) SEQUENCE CHARACTERISTICS:
        (A) LENGTH: 407 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

```
CCGCCACCAT GGGATGGAGC TGGATCTTTA TCTTCCTCCT CTCAGTAATT GCAGGTGTCC      60
AATCCCAGGT TCAACTGCAG CAGTCTGGGA CTGAACTGGT GAGGCCTGGG GCTTCAGTGA     120
CGCTGTCCTG CAAGGCTTCG GGCTACACAT TTACTGACCA TGAAATGCAC TGGGTGAAGC     180
AGACACCTGT GCTTGGCCTG GAATGGATTG GAACTATTGA TCCTGAAACT GGTGGTACTG     240
CCTACAATCA GAAGTTCAAG GGCAAGGCCA CACTGACTGC AGACAAATCC TCCACTACAG     300
CCTACATGGA CCTCCGCGGC CTGACATCTG AGGACTCTGC CGTCTTTTAC TGTACAGTCC     360
TAAGGATGGA CTACTGGGGT CAAGGAACCT CACTCACAGT CTCCGCA                   407
```

(2) INFORMATION FOR SEQ ID NO: 6:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

| Met | Gly | Trp | Ser | Trp | Ile | Phe | Ile | Phe | Leu | Leu | Ser | Val | Ile | Ala | Gly |
|---|---|---|---|---|---|---|---|---|---|---|---|---|---|---|---|
| 1 | | | | 5 | | | | | 10 | | | | | 15 | |

| Val | Gln | Ser | Gln | Val | Gln | Leu | Gln | Gln | Ser | Gly | Thr | Glu | Leu | Val | Arg |
|---|---|---|---|---|---|---|---|---|---|---|---|---|---|---|---|
| | | | 20 | | | | | 25 | | | | | 30 | | |

| Pro | Gly | Ala | Ser | Val | Thr | Leu | Ser | Cys | Lys | Ala | Ser | Gly | Tyr | Thr | Phe |

```
                    35                  40                  45
Thr Asp His Glu Met His Trp Val Lys Gln Thr Pro Val Leu Gly Leu
 50                  55                  60

Glu Trp Ile Gly Thr Ile Asp Pro Glu Thr Gly Gly Thr Ala Tyr Asn
 65                  70                  75                  80

Gln Lys Phe Lys Gly Lys Ala Thr Leu Thr Ala Asp Lys Ser Ser Thr
                 85                  90                  95

Thr Ala Tyr Met Asp Leu Arg Gly Leu Thr Ser Glu Asp Ser Ala Val
                100                 105                 110

Phe Tyr Cys Thr Val Leu Arg Met Asp Tyr Trp Gly Gln Gly Thr Ser
                115                 120                 125

Leu Thr Val Ser Ala
    130

(2) INFORMATION FOR SEQ ID NO: 7:

(i) SEQUENCE CHARACTERISTICS:
        (A) LENGTH: 420 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

GCGCGCAAGC TTGCCGCCAC CATGGAATGG AGCTGGGTCT TTCTCTTCTT CCTGTCAGTA     60

ACTACAGGAG TCCATTCTCA GGTGCAGCTG GTGCAGTCTG GAGCAGAGGT GAAGAAGCCT    120

GGATCTTCTG TGAAGGTGTC TTGTAAGGCA TCTGGATACA CATTCACAGA CCACGAGATG    180

CACTGGGTGA GACAGGCACC TGGACAGGGA CTCGAGTGGA TTGGAACAAT TGACCCTGAG    240

ACAGGAGGAA CAGCCTACAA TCAGAAGTTC AAGGGAAGAG CAAACACTGAC AGCAGACAAG   300

TCTACGAATA CCGCCTACAT GGAGCTGTCT TCTCTGAGAT CTGAGGACAC AGCAGTGTAC    360

TACTGTACAG TGCTCAGAAT GGACTACTGG GGACAGGGAA CACTGGTGAC AGTGTCTTCT    420

(2) INFORMATION FOR SEQ ID NO: 8:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Glu Trp Ser Trp Val Phe Leu Phe Phe Leu Ser Val Thr Thr Gly
 1                   5                  10                  15

Val His Ser Gln Val Gln Leu Val Gln Ser Gly Ala Glu Val Lys Lys
                 20                  25                  30

Pro Gly Ser Ser Val Lys Val Ser Cys Lys Ala Ser Gly Tyr Thr Phe
                 35                  40                  45

Thr Asp His Glu Met His Trp Val Arg Gln Ala Pro Gly Gln Gly Leu
 50                  55                  60

Glu Trp Ile Gly Thr Ile Asp Pro Glu Thr Gly Gly Thr Ala Tyr Asn
 65                  70                  75                  80

Gln Lys Phe Lys Gly Arg Ala Thr Leu Thr Ala Asp Lys Ser Thr Asn
                 85                  90                  95

Thr Ala Tyr Met Asp Leu Ser Ser Leu Arg Ser Glu Asp Thr Ala Val
```

100                 105                 110
Tyr Tyr Cys Thr Val Leu Arg Met Asp Tyr Trp Gly Gln Gly Thr Leu
            115                 120                 125
Val Thr Val Ser Ser
        130

(2) INFORMATION FOR SEQ ID NO: 9:

(i) SEQUENCE CHARACTERISTICS:
        (A) LENGTH: 423 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

GGACTGTTCG AAGCCGCCAC CATGTCTGTC CCCACCCAAG TCCTCGGACT CCTGCTGCTG      60

TGGCTTACAG ATGCCAGATG CGATATCCAG ATGACTCAGA GTCCAAGTAC TCTCAGTGCC     120

AGTGTAGGTG ATAGGGTCAC CATCACTTGT AAGTCTTCTC AATCTCTCTT AAACTCCGGT     180

AACCAGCAGA ACTACCTCAC TTGGTACCAG CAGAAACCAC CAGGTAAAGC CCCAAAGCTC     240

CTCATCTATT GGGCCTCTAC TAGGGAATCT GGTGTACCAG ATAGATTCAC TGGTAGTGGT     300

AGTGGTACTG ATTTCACTCT CACTATCAGT AGTCTCCAGG ATGATTTCGC CACTTATTAC     360

TGTCAGAACG ATTACGATTA CCCATTAACT TTCGGTCAGG GTACTAAAGT AGAAATCAAA     420

CGT                                                                  423

(2) INFORMATION FOR SEQ ID NO: 10:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Thr Leu Ser
            20                  25                  30

Ala Ser Val Gly Asp Arg Val Thr Ile Thr Cys Lys Ser Ser Gln Ser
            35                  40                  45

Leu Leu Asn Ser Gly Asn Gln Gln Asn Tyr Leu Thr Trp Tyr Gln Gln
        50                  55                  60

Lys Pro Gly Lys Ala Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
            85                  90                  95

Phe Thr Leu Thr Ile Ser Ser Leu Gln Pro Asp Asp Phe Ala Val Tyr
            100                 105                 110

Tyr Cys Gln Asn Asp Tyr Asp Tyr Pro Leu Thr Phe Gly Gln Gly Thr
            115                 120                 125

Lys Val Glu Ile Lys Arg
        130

(2) INFORMATION FOR SEQ ID NO:11:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:11:

Ala Pro Glu Leu Leu Gly Gly Pro Ser Val Phe Leu Phe Pro Pro Lys
1               5                   10                  15

Asp Thr (2) INFORMATION FOR SEQ ID NO:12:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:12:

Ala Pro Pro Val Ala Gly Pro Ser Val Phe Leu Phe Pro Pro Lys Asp
1               5                   10                  15

Thr (2) INFORMATION FOR SEQ ID NO:13:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:13:

Ala Pro Glu Leu Leu Gly Gly Pro Ser Val Phe Leu Phe Pro Pro Lys
1               5                   10                  15

Asp Thr (2) INFORMATION FOR SEQ ID NO:14:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:14:

Ala Pro Glu Phe Leu Gly Gly Pro Ser Val Phe Leu Phe Pro Pro Lys
1               5                   10                  15

Asp Thr (2) INFORMATION FOR SEQ ID NO:15:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:15:

Ala Pro Glu Phe Ile Gly Gly Pro Ser Val
1               5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Ala Pro Glu Phe Ala Gly Gly Pro Ser Val
1               5                   10

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Ala Pro Glu Phe Val Gly Gly Pro Ser Val
1               5                   10

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Ala Pro Glu Phe Thr Gly Gly Pro Ser Val
1               5                   10

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Mutagenic oligonucleotide"

(xi) SEQUENCE DESCRIPTION: SEQ ID NO: 19:

CCTGAGTTCG TCGGGGGACC ATCAGTCTTC                                          30

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear -continued

```
    (ii) MOLECULE TYPE: other nucleic acid
        (A) DESCRIPTION:  /desc = "Mutagenic oligonucleotide"

(xi) SEQUENCE DESCRIPTION: SEQ ID NO: 20:

GAAGGAGTCG TGGACTCAAG CAGCCCCCTG G                                   31

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Mutagenic oligonucleotide"

(xi) SEQUENCE DESCRIPTION: SEQ ID NO: 21:

CCTGAGTTCA CCGGGGGACC ATCAGTCTTC                                     30

(2) INFORMATION FOR SEQ ID NO: 22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "Mutagenic oligonucleotide"

(xi) SEQUENCE DESCRIPTION: SEQ ID NO: 22:

GAAGGAGTCG TGGACTCAAG TGGCCCCCTG G                                   31
```